(12) United States Patent
Urch et al.

(10) Patent No.: US 11,634,390 B2
(45) Date of Patent: Apr. 25, 2023

(54) AGRICULTURAL CHEMICALS

(71) Applicant: GLOBACHEM NV, Sint-Truiden (BE)

(72) Inventors: Christopher John Urch, Alderley Edge (GB); Victoria Elizabeth Jackson, Alderley Edge (GB); Calum William Muir, Alderley Edge (GB)

(73) Assignee: GLOBACHEM NV, Sint-Truiden (BE)

( * ) Notice: Subject to any disclaimer, the term of this patent is extended or adjusted under 35 U.S.C. 154(b) by 191 days.

(21) Appl. No.: 16/465,222

(22) PCT Filed: Dec. 28, 2017

(86) PCT No.: PCT/GB2017/053898
§ 371 (c)(1),
(2) Date: May 30, 2019

(87) PCT Pub. No.: WO2018/122559
PCT Pub. Date: Jul. 5, 2018

(65) Prior Publication Data
US 2019/0322627 A1    Oct. 24, 2019

(30) Foreign Application Priority Data
Dec. 29, 2016  (GB) ..................... 1622345

(51) Int. Cl.
| | | |
|---|---|---|
| *C07D 239/10* | (2006.01) | |
| *C07D 401/12* | (2006.01) | |
| *C07D 403/12* | (2006.01) | |
| *C07D 405/12* | (2006.01) | |
| *C07D 409/12* | (2006.01) | |
| *A01N 43/54* | (2006.01) | |

(52) U.S. Cl.
CPC ........... *C07D 239/10* (2013.01); *A01N 43/54* (2013.01); *C07D 401/12* (2013.01); *C07D 403/12* (2013.01); *C07D 405/12* (2013.01); *C07D 409/12* (2013.01)

(58) Field of Classification Search
CPC .............................. C07D 239/10; A01N 43/54
See application file for complete search history.

(56) References Cited

U.S. PATENT DOCUMENTS

| | | | |
|---|---|---|---|
| 2004/0220172 A1 | 11/2004 | Carlsen et al. | |
| 2011/0257151 A1* | 10/2011 | Chen | C07D 215/18 544/405 |
| 2013/0102463 A1* | 4/2013 | Ehrhardt | A01N 43/54 504/103 |
| 2016/0214945 A1 | 7/2016 | Urch et al. | |

FOREIGN PATENT DOCUMENTS

| | | | | |
|---|---|---|---|---|
| WO | WO-0183459 A2 * | 11/2001 | ............. | A01N 41/02 |
| WO | 2003029226 A1 | 4/2003 | | |
| WO | WO-2007042447 A2 * | 4/2007 | ............. | A01N 43/54 |
| WO | WO-2011064533 A2 * | 6/2011 | ............. | A01N 43/54 |
| WO | WO-2011161105 A2 * | 12/2011 | ............. | A01N 25/22 |
| WO | WO-2015040409 A2 * | 3/2015 | ........... | A01N 43/653 |

OTHER PUBLICATIONS

International Search Report and the Written Opinion for International Application No. PCT/GB2017/053898, dated Feb. 13, 2018, 24 pages.
Search Report issued in GB Patent Application No. GB1622345.5, dated Oct. 2, 2017, 4 pages.

* cited by examiner

*Primary Examiner* — Alton N Pryor
(74) *Attorney, Agent, or Firm* — Morgan, Lewis & Bockius, LLP

(57) ABSTRACT

The present invention relates to compounds which are of use in the field of agriculture as herbicides. The invention also relates to methods of using said compounds and compositions comprising said compounds.

27 Claims, No Drawings

AGRICULTURAL CHEMICALS

This application is the U.S. national stage application of International (PCT) Patent Application Serial No. PCT/GB2017/053898, filed Dec. 28, 2017, which claims the benefit of GB Application No. 1622345.5, filed Dec. 29, 2016. The entire disclosure of each of these applications is hereby incorporated by reference.

The present invention relates to compounds which are of use in the field of agriculture as herbicides.

Given the global increase in demand for food, there is an international need for new treatments to reduce food crop losses to disease, insects and weeds. Over 40% of crops are lost before harvest, and 10% post harvest, worldwide. Losses have actually increased since the mid-1990s.

Saflufenacil is a herbicide used to control annual broadleaf weeds in soybeans and maize.

WO2015/040409 describes a series of compounds similar to saflufenacil and their herbicidal activities.

It is an aim of certain embodiments of the invention to provide herbicidal compounds that are more active than prior art compounds. It is an aim of certain embodiments of the invention to provide herbicidal compounds that are more selective than prior art compounds, i.e. they may have better, similar or even lower activity than prior art compounds against target plant species but are significantly less active against non-target plant species (e.g. the crops which are being protected).

This invention provides compounds that achieve one or more of the above aims.

SUMMARY OF THE INVENTION

In a first aspect of the invention is provided a compound of formula I:

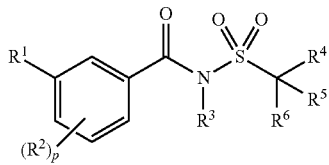

I wherein
$R^1$ is selected from 5- to 9-membered bicyclic or monocyclic heterocycloalkyl group and 5-, 6-, 9- or 10-membered heteroaryl group; wherein said heterocycloalkyl or heteroaryl group comprises at least one nitrogen atom in the ring and is optionally substituted with from 1 to 6 $R^7$ groups; or wherein $R^1$ is —N=$CR^8R^9$ wherein $R^8$ and $R^9$ together with the carbon atom to which they are attached form a 5- to 9-membered bicyclic or monocyclic heterocycloalkyl group; wherein said heterocycloalkyl group comprises at least one nitrogen atom in the ring and is optionally substituted with from 1 to 6 $R^7$ groups;
$R^2$ is independently at each occurrence selected from $C_1$-$C_6$-alkyl, $C_1$-$C_6$-haloalkyl, halogen, nitro, $OR^{10}$, $SR^{10}$, $OS(O)_2R^{10}$, $S(O)_2R^{10}$, $S(O)_2NR^{10}R^{10}$, $S(O)(NR^{10})R^{10}$, $S(O)R^{10}$, cyano, $C_2$-$C_6$-alkenyl, $C_2$-$C_6$-alkynyl, $C_3$-$C_6$-cycloalkyl, $C_3$-$C_6$-heterocycloalkyl and $NR^{10}R^{11}$;
$R^3$ is independently selected from: H, $C_1$-$C_6$-alkyl and $C_3$-$C_6$-cycloalkyl;
$R^4$ is independently selected from H, fluoro, chloro, $C_1$-$C_6$-haloalkyl and $C_1$-$C_6$-alkyl;

$R^5$ and $R^6$ together with the carbon atom to which they are attached form a cyclic group selected from $C_3$-$C_8$-cycloalkyl and 4- to 8-membered heterocycloalkyl; wherein the cyclic group is optionally substituted with from 1 to 4 $R^{12}$ groups;
$R^7$ and $R^{12}$ are independently at each occurrence selected from: =O, =S, $C_1$-$C_6$-alkyl, $C_1$-$C_6$-haloalkyl, halogen, nitro, $OR^{10}$, $SR^{10}$, $S(O)_2R^{10}$, $S(O)_2NR^{10}R^{10}$, $S(O)(NR^{10})R^{10}$, $S(O)R^{10}$, $C(O)R^{10}$, $C(O)NR^{10}R^{10}$, $C(O)OR^{10}$, cyano, $C_2$-$C_6$-alkenyl, $C_2$-$C_6$-alkynyl, $C_3$-$C_6$-cycloalkyl, 3- to 6-membered heterocycloalkyl and $NR^{10}R^{11}$;
$R^{10}$ is independently at each occurrence selected from: H and $C_1$-$C_6$-alkyl;
$R^{11}$ is independently at each occurrence selected from; H, $C_1$-$C_6$-alkyl, $C(O)$—$C_1$-$C_6$-alkyl and $S(O)_2$—$C_1$-$C_6$-alkyl;
p is an integer independently selected from 0, 1, 2 and 3;
wherein any $R^2$, $R^3$, $R^4$, $R^7$, $R^{10}$, $R^{11}$ or $R^{12}$ group that is alkyl, cycloalkyl, or heterocycloalkyl is optionally substituted, where chemically possible, by 1 to 4 substituents which are each independently selected at each occurrence from the group consisting of: =O; =$NR^a$, =$NOR^a$, $C_1$-$C_6$-alkyl, halo, nitro, cyano, $C_1$-$C_6$-haloalkyl, $C_2$-$C_6$-alkenyl, $C_2$-$C_6$-alkynyl, $NR^aR^b$, $S(O)_2R^a$, $S(O)R^a$, $S(O)(NR^a)R^a$, $S(O)_2NR^aR^a$, $CO_2R^a$, $C(O)R^a$, $CONR^aR^a$ and $OR^a$;
wherein $R^a$ is independently selected from H and $C_1$-$C_4$-alkyl; and $R^b$ is independently H, $C_1$-$C_6$-alkyl, $C(O)$—$C_1$-$C_6$-alkyl, $S(O)_2$—$C_1$-$C_6$-alkyl or an agronomically acceptable salt or N-oxide thereof.

In an embodiment, the compound of formula I is a compound of formula II:

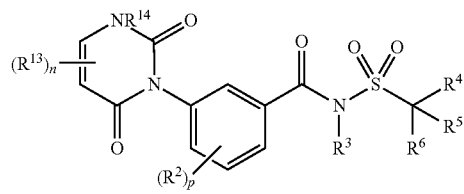

II wherein $R^2$, $R^3$, $R^4$, $R^5$, $R^6$ and p are as described above for compounds of formula I; and wherein $R^{13}$ is independently at each occurrence selected from $C_1$-$C_6$-alkyl, $C_1$-$C_6$-haloalkyl, halogen, nitro, $OR^{10}$, $SR^{10}$, cyano, $C_2$-$C_6$-alkenyl, $C_2$-$C_6$-alkynyl, $C_3$-$C_6$-cycloalkyl and $NR^{10}R^{11}$; $R^{14}$ is independently selected from H and $C_1$-$C_6$-alkyl; and n is an integer independently selected from 0, 1 and 2.

In an embodiment, the compound of formula I is a compound of formula III:

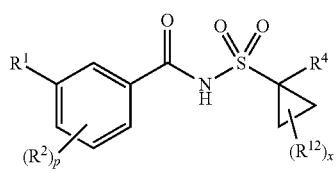

III wherein $R^1$, $R^2$, $R^4$, $R^{12}$ and p are as described above for compounds of formula I; and wherein x is an integer selected from 0, 1, 2, 3 and 4.

In an embodiment, the compound of formula I is a compound of formula IV:

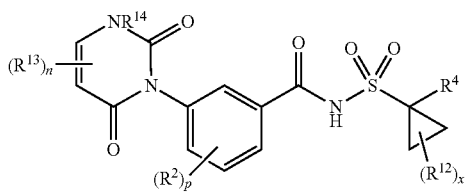

wherein $R^2$, $R^4$, $R^{12}$ and p are as described above for compounds of formula I; and wherein $R^{13}$, $R^{14}$ and n are as described above for compounds of formula II; and wherein x is an integer selected from 0, 1, 2, 3 and 4.

In an embodiment, the compound of formula I is a compound of formula V:

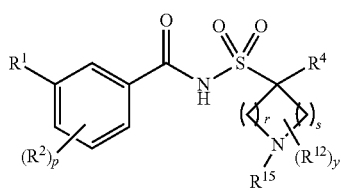

wherein $R^1$, $R^2$, $R^4$, $R^{12}$ and p are as described above for compounds of formula I; and wherein $R^{15}$ is independently selected from H, $C_1$-$C_6$-alkyl, —C(O)—$C_1$-$C_6$-alkyl, $CONR^{10}R^{10}$ and —$S(O)_2$—$C_1$-$C_6$-alkyl; y is an integer selected from 0, 1, 2 and 3; r and s are each an integer selected from 0, 1, 2, 3 and 4; and wherein the sum of r and s is 2, 3 or 4.

In an embodiment, the compound of formula I is a compound of formula VI:

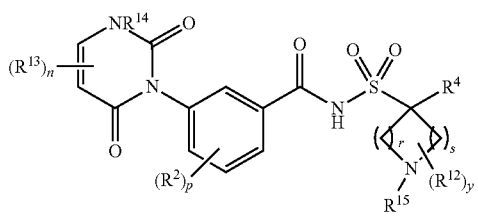

wherein $R^2$, $R^4$, $R^{12}$ and p are as described above for compounds of formula I; and wherein $R^{13}$, $R^{14}$ and n are as described above for compounds of formula II; and wherein $R^{15}$, r, s and y are as described above for compounds of formula V.

In an embodiment, the compound of formula I is a compound of formula VII:

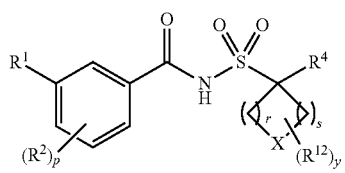

wherein $R^1$, $R^2$, $R^4$, $R^{12}$ and p are as described above for compounds of formula I; and wherein r, s and y are as described above for compounds of formula V; and X is selected from: O or $S(=O)_z$; wherein z is 0, 1 or 2.

In an embodiment, the compound of formula I is a compound of formula VIII:

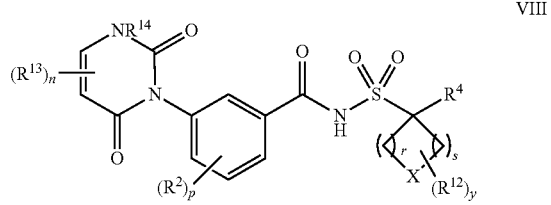

wherein $R^2$, $R^4$, $R^{12}$ and p are as described above for compounds of formula I; and wherein $R^{13}$, $R^{14}$ and n are as described above for compounds of formula II; and wherein r, s and y are as described above for compounds of formula V; and X is selected from: O or $S(=O)_z$; wherein z is 0, 1 or 2.

The following embodiments apply to compounds of any of formulae (I)-(VIII). These embodiments are independent and interchangeable. Any one embodiment may be combined with any other embodiment, where chemically allowed. In other words, any of the features described in the following embodiments may (where chemically allowable) be combined with the features described in one or more other embodiments. In particular, where a compound is exemplified or illustrated in this specification, any two or more of the embodiments listed below, expressed at any level of generality, which encompass that compound may be combined to provide a further embodiment which forms part of the present disclosure.

It may be that $R^1$ is selected from 5- to 9-membered bicyclic or monocyclic heterocycloalkyl group and 5-, 6-, 9- or 10-membered heteroaryl group; wherein said heterocycloalkyl or heteroaryl group comprises at least one nitrogen atom in the ring and is optionally substituted with from 1 to 6 $R^7$ groups.

$R^1$ may be a 5- to 9-membered bicyclic or monocyclic heterocycloalkyl group, wherein said heterocycloalkyl group comprises at least one nitrogen atom in the ring and is optionally substituted with from 1 to 6 $R^7$ groups. $R^1$ may have the structure:

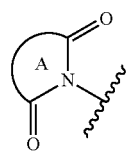

wherein ring A is a 5- or 6-membered heterocycloalkyl group, which is optionally fused to a 5- or 6-membered cycloalkyl or heterocycloalkyl ring and wherein the group $R^1$ is optionally substituted with from 1 to 4 $R^7$ groups. Ring A may be a 5- or 6-membered heterocycloalkyl group, which is optionally substituted with from 1 to 4 $R^7$ groups.

$R^1$ may be

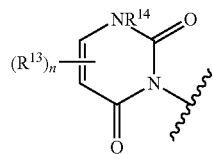

wherein $R^{13}$ is independently at each occurrence selected from $C_1$-$C_6$-alkyl, $C_1$-$C_6$-haloalkyl, halogen, nitro, $OR^{10}$, $SR^{10}$, cyano, $C_2$-$C_6$-alkenyl, $C_2$-$C_6$-alkynyl, $C_3$-$C_6$-cycloalkyl and $NR^{10}R^{11}$;

$R^{14}$ is independently selected from H and $C_1$-$C_6$-alkyl; and n is an integer independently selected from 0, 1 and 2.

It may be that n is 1. $R^{13}$ may be independently at each occurrence selected from: $C_1$-$C_6$-alkyl, $C_1$-$C_6$-haloalkyl and halogen. $R^{13}$ may be independently at each occurrence selected from: $C_1$-$C_6$-alkyl and $C_1$-$C_6$-haloalkyl. Thus, $R^{13}$ may be $C_1$-$C_6$-haloalkyl, e.g. $CF_3$.

$R^{14}$ may be $C_1$-$C_6$-alkyl. Preferably, $R^{14}$ is methyl.

In certain illustrative examples, $R^1$ may be:

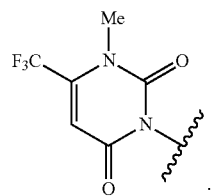

$R^1$ may have the structure:

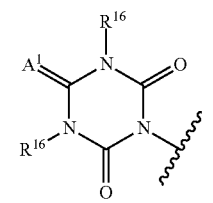

wherein $=A^1$ is independently selected from $=O$ and $=S$; and $R^{16}$ is independently at each occurrence selected from H and $C_1$-$C_6$-alkyl.

$=A^1$ may be $=O$. $=A^1$ may be $=S$. $R^{16}$ may be at both occurrences $C_1$-$C_6$-alkyl, e.g. Me.

In certain illustrative examples, $R^1$ may be:

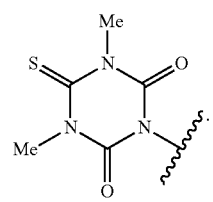

Other illustrative examples of $R^1$ include:

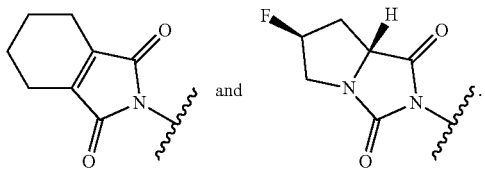 [SMILES: *N1C(=O)C2=C(CCCC2)C1=O ; *N1C(=O)[C@H]2C[C@H](F)CN2C1=O]

$R^1$ may have the structure:

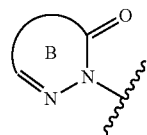

wherein ring B is a 5- or 6-membered heterocycloalkyl group, which is optionally fused to a 5- or 6-membered cycloalkyl or heterocycloalkyl ring and wherein the group $R^1$ is optionally substituted with from 1 to 5 $R^7$ groups. Ring B may be a 5- or 6-membered heterocycloalkyl group, which is optionally substituted with from 1 to 5 $R^7$ groups.

Illustrative examples of $R^1$ include:

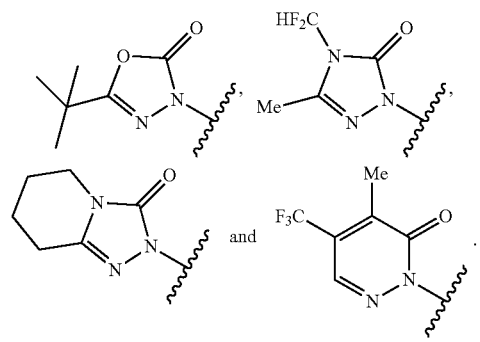

It may be that $R^1$ is 5-, 6-, 9- or 10-membered heteroaryl group; wherein said heteroaryl group comprises at least one nitrogen atom in the ring and is optionally substituted with from 1 to 6 $R^7$ groups. It may be that $R^1$ is 5- or 6-membered heteroaryl group; wherein said heteroaryl group comprises at least one nitrogen atom in the ring and is optionally substituted with from 1 to 5 $R^7$ groups. It may be that $R^1$ is 5-membered heteroaryl group; wherein said heteroaryl group comprises at least one nitrogen atom in the ring and is optionally substituted with from 1 to 4 $R^7$ groups. It may be that $R^1$ is a pyrazole, e.g. a 3-pyrazole.

Thus, $R^1$ may have the structure:

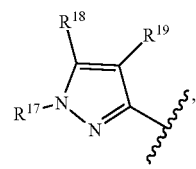

wherein $R^{17}$ is independently selected from H and $C_1$-$C_6$-alkyl; and $R^{18}$ and $R^{19}$ are each independently selected from $C_1$-$C_6$-alkyl, $C_1$-$C_6$-haloalkyl, O—$C_1$-$C_6$-alkyl and halogen.

$R^{17}$ may be $C_1$-$C_6$-alkyl, e.g. Me. $R^{18}$ may be $C_1$-$C_6$-haloalkyl or O—$C_1$-$C_6$-alkyl. $R^{19}$ may be halogen.

Illustrative examples of $R^1$ include:

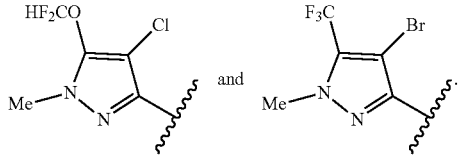

and $R^1$ may be —N=$CR^8R^9$ wherein $R^8$ and $R^9$ together with the carbon atom to which they are attached form a 5- to 9-membered bicyclic or monocyclic heterocycloalkyl group; wherein said heterocycloalkyl group comprises at least one nitrogen atom in the ring and is optionally substituted with from 1 to 6 $R^7$ groups.

$R^1$ may have the structure:

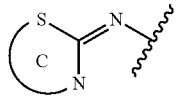

wherein ring C is a 5- or 6-membered heterocycloalkyl group, which is optionally fused to a 5- or 6-membered cycloalkyl or heterocycloalkyl ring and wherein the group $R^1$ is optionally substituted with from 1 to 5 $R^7$ groups. It may be that ring C is a 5- or 6-membered heterocycloalkyl group which is fused to a 5- or 6-membered cycloalkyl or heterocycloalkyl ring and wherein the group $R^1$ is optionally substituted with from 1 to 5 $R^7$ groups.

Illustrative examples of $R^1$ include:

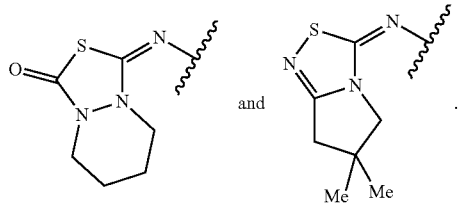 [SMILES: */N=c1/sc(=O)n2n1CCCC2 ; */N=c1/snc2n1CC(C)(C)C2]

and $R^7$ may be independently at each occurrence selected from: =O, =S, $C_1$-$C_6$-alkyl, $C_1$-$C_6$-haloalkyl and halogen. $R^7$ may be independently at each occurrence selected from: $C_1$-$C_6$-alkyl, $C_1$-$C_6$-haloalkyl and halogen.

p may be 1 or p may be 2. $R^2$ may be independently at each occurrence selected from: $C_1$-$C_6$-alkyl, cyano, nitro, $C_1$-$C_6$-haloalkyl and halogen. $R^2$ may be independently at each occurrence selected from: $C_1$-$C_6$-alkyl, $C_1$-$C_6$-haloalkyl and halogen. It may be that $R^2$ is at each occurrence halogen. Said halogen substituents may be the same or different. If, for example, p is 2, $R^2$ may be at both occurrences F. As another example, if p is 2, $R^2$ may be at one occurrence Cl and at the other occurrence F. Likewise, where p is 1, $R^2$ may be F. Alternatively, $R^2$ may be Cl.

The group:

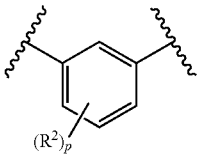

may have the structure:

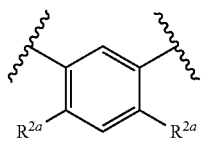

wherein $R^{2a}$ is independently at each occurrence selected from: H, $C_1$-$C_6$-alkyl, cyano, nitro, $C_1$-$C_6$-haloalkyl and halogen. $R^{2a}$ may be independently at each occurrence selected from: $C_1$-$C_6$-alkyl, $C_1$-$C_6$-haloalkyl and halogen. It may be that $R^{2a}$ is at each occurrence selected from H and halogen. It may be that $R^{2a}$ is at each occurrence halogen.

$R^3$ is preferably H.

$R^4$ may be H. $R^4$ may be selected from H, fluoro and chloro. $R^4$ may be F.

$R^4$ may be independently selected from fluoro, chloro, $C_1$-$C_6$-haloalkyl and $C_1$-$C_6$-alkyl. $R^4$ may be independently selected from $C_1$-$C_6$-haloalkyl and $C_1$-$C_6$-alkyl. Thus, $R^4$ may be selected from Me, Et and $CF_3$. $R^4$ may be $C_1$-$C_6$-alkyl, e.g. Me or Et.

$R^5$ and $R^6$ may together with the carbon atom to which they are attached form a $C_3$-$C_8$-cycloalkyl group; wherein the cycloalkyl group is optionally substituted with from 1 to 4 $R^{12}$ groups. Thus, $R^5$ and $R^6$ may together with the carbon atom to which they are attached form a $C_3$-$C_6$-cycloalkyl group; wherein the cycloalkyl group is optionally substituted with from 1 to 4 $R^{12}$ groups.

$R^5$ and $R^6$ may together with the carbon atom to which they are attached form a cyclopropyl group; wherein the cyclopropyl group is optionally substituted with from 1 to 3 $R^{12}$ groups. $R^5$ and $R^6$ may together with the carbon atom to which they are attached form an unsubstituted cyclopropyl group.

$R^5$ and $R^6$ may together with the carbon atom to which they are attached form a cyclobutyl group; wherein the cyclobutyl group is optionally substituted with from 1 to 4 $R^{12}$ groups. $R^5$ and $R^6$ may together with the carbon atom to which they are attached form an unsubstituted cyclobutyl group.

$R^5$ and $R^6$ may together with the carbon atom to which they are attached form a cyclopentyl group; wherein the cyclopentyl group is optionally substituted with from 1 to 4 $R^{12}$ groups. $R^5$ and $R^6$ may together with the carbon atom to which they are attached form an unsubstituted cyclopentyl group.

$R^5$ and $R^6$ may together with the carbon atom to which they are attached form a cyclohexyl group; wherein the cyclohexyl group is optionally substituted with from 1 to 4 $R^{12}$ groups. $R^5$ and $R^6$ may together with the carbon atom to which they are attached form an unsubstituted cyclohexyl group.

$R^5$ and $R^6$ together with the carbon atom to which they are attached may form a 4- to 8-membered heterocycloalkyl group; wherein the heterocycloalkyl group is optionally substituted with from 1 to 4 $R^{12}$ groups. $R^5$ and $R^6$ together with the carbon atom to which they are attached may form a 4- to 6-membered heterocycloalkyl group; wherein the heterocycloalkyl group is optionally substituted with from 1 to 4 $R^{12}$ groups.

$R^5$ and $R^6$ may, together with the carbon to which they are attached have the structure:

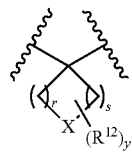

X is selected from: $NR^{15}$, O or $S(=O)_z$; $R^{15}$ is independently selected from H, $C_1$-$C_6$-alkyl, —C(O)—$C_1$-$C_6$-alkyl and —$S(O)_2$—$C_1$-$C_6$-alkyl; z is 0, 1 or 2; y is an integer selected from 0, 1, 2 and 3; r and s are each an integer selected from 0, 1, 2, 3 and 4; and wherein the sum of r and s is 2, 3 or 4.

$R^5$ and $R^6$ together with the carbon atom to which they are attached may form a 4-membered heterocycloalkyl group; wherein the heterocycloalkyl group is optionally substituted with from 1 to 4 $R^{12}$ groups. It may be that r is 1 and s is 1. It may be that r is 0 and s is 2.

$R^5$ and $R^6$ together with the carbon atom to which they are attached may form a 5-membered heterocycloalkyl group; wherein the heterocycloalkyl group is optionally substituted with from 1 to 4 $R^{12}$ groups. It may be that r is 1 and s is 2. It may be that r is 0 and s is 3.

$R^5$ and $R^6$ together with the carbon atom to which they are attached may form a 6-membered heterocycloalkyl group; wherein the heterocycloalkyl group is optionally substituted with from 1 to 4 $R^{12}$ groups. It may be that r is 2 and s is 2. It may be that r is 1 and s is 3. It may be that r is 0 and s is 4.

It may be that X is $NR^{15}$. It may be that X is $NR^{15}$, r is 1 and s is 1. It may be that X is $NR^{15}$, r is 0 and s is 2. It may be that X is $NR^{15}$, r is 1 and s is 2. It may be that X is $NR^{15}$, r is 0 and s is 3.

It may be that X is $NR^{15}$, r is 2 and s is 2. It may be that X is $NR^{15}$, r is 1 and s is 3. It may be that X is $NR^{15}$, r is 0 and s is 4. It may be that $R^{15}$ is selected from H and $C_1$-$C_6$-alkyl. It may be that $R^{15}$ is H. It may be that $R^{15}$ is $C_1$-$C_6$-alkyl, e.g. Me.

It may be that X is O or S. It may be that X is O. It may be that X is S. It may be that X is O, r is 1 and s is 1. It may be that X is O, r is 0 and s is 2. It may be that X is O, r is 1 and s is 2. It may be that X is O, r is 0 and s is 3. It may be that X is O, r is 2 and s is 2. It may be that X is O, r is 1 and s is 3. It may be that X is O, r is 0 and s is 4. It may be that X is S, r is 1 and s is 1. It may be that X is S, r is 0 and s is 2. It may be that X is S, r is 1 and s is 2. It may be that X is S, r is 0 and s is 3. It may be that X is S, r is 2 and s is 2. It may be that X is S, r is 1 and s is 3. It may be that X is S, r is 0 and s is 4.

It may be that X is $SO_2$. It may be that X is $SO_2$, r is 1 and s is 1. It may be that X is $SO_2$, r is 0 and s is 2. It may be that X is $SO_2$, r is 1 and s is 2. It may be that X is $SO_2$, r is 0 and s is 3. It may be that X is $SO_2$, r is 2 and s is 2. It may be that X is $SO_2$, r is 1 and s is 3. It may be that X is $SO_2$, r is 0 and s is 4.

y may be 0. y may be 1. If present, $R^{12}$ may at each occurrence be selected from $C_1$-$C_6$-alkyl and $C_1$-$C_6$-haloalkyl.

The compound of formula (I) may be selected from:

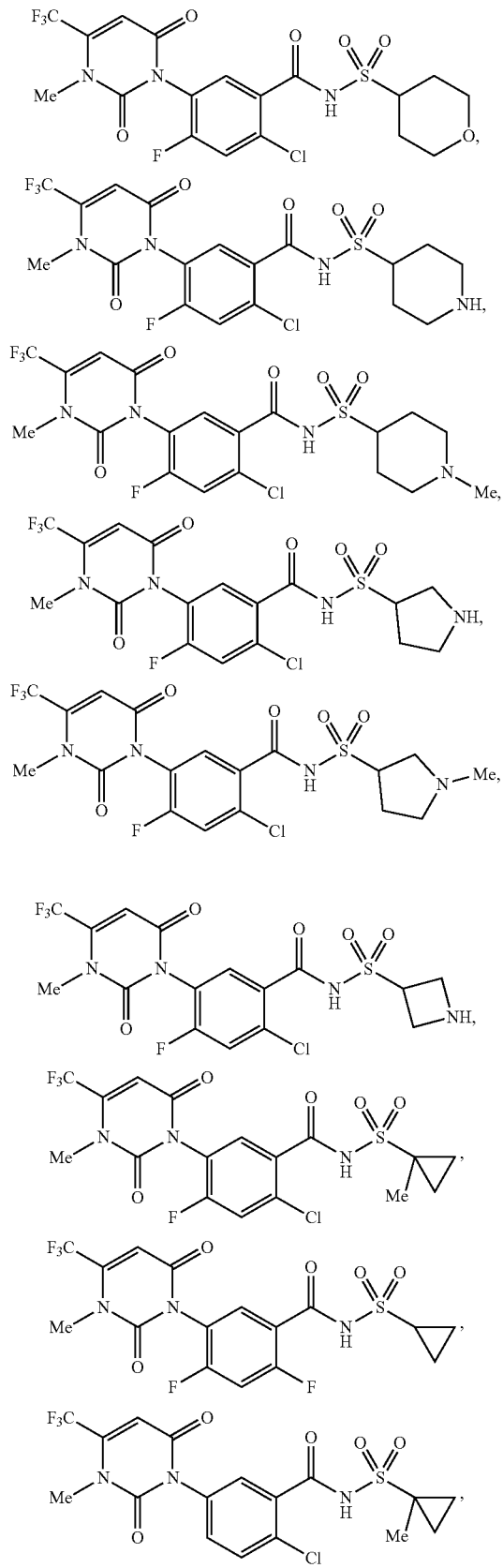

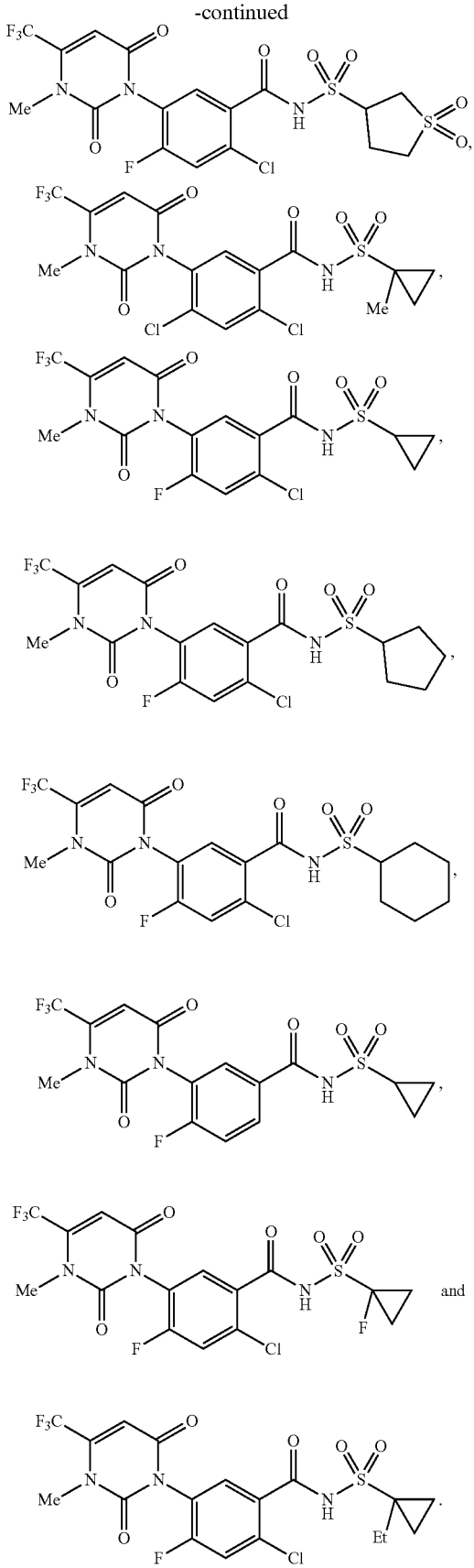

The invention may be as described in any of the following numbered paragraphs:

1. A compound of formula I:

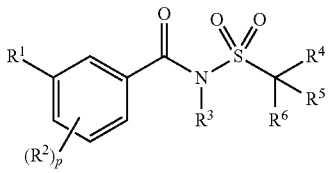

wherein $R^1$ is selected from 5- to 9-membered bicyclic or monocyclic heterocycloalkyl group and 5-, 6-, 9- or 10-membered heteroaryl group; wherein said heterocycloalkyl or heteroaryl group comprises at least one nitrogen atom in the ring and is optionally substituted with from 1 to 6 $R^7$ groups; or wherein $R^1$ is —N=$CR^8R^9$ wherein $R^8$ and $R^9$ together with the carbon atom to which they are attached form a 5- to 9-membered bicyclic or monocyclic heterocycloalkyl group; wherein said heterocycloalkyl group comprises at least one nitrogen atom in the ring and is optionally substituted with from 1 to 6 $R^7$ groups;

$R^2$ is independently at each occurrence selected from $C_1$-$C_4$-alkyl, $C_1$-$C_4$-haloalkyl, halogen, nitro, $OR^{10}$, $SR^{10}$, $OS(O)_2R^{10}$, $S(O)_2R^{10}$, $S(O)_2NR^{10}R^{10}$, $S(O)(NR^{10})R^{10}$, $S(O)R^{10}$, cyano, $C_2$-$C_4$-alkenyl, $C_2$-$C_4$-alkynyl, $C_3$-$C_6$-cycloalkyl, $C_3$-$C_6$-heterocycloalkyl and $NR^{10}R^{11}$;

$R^3$ is independently selected from: H and $C_1$-$C_4$-alkyl and $C_3$-$C_6$-cycloalkyl;

$R^4$ is independently selected from H, fluoro, chloro, $C_1$-$C_4$-haloalkyl and $C_1$-$C_4$-alkyl;

$R^5$ and $R^6$ together with the carbon atom to which they are attached form a cyclic group selected from $C_3$-$C_8$-cycloalkyl and 4- to 8-membered heterocycloalkyl; wherein the cyclic group is optionally substituted with from 1 to 4 $R^{12}$ groups;

$R^7$ and $R^{12}$ are independently at each occurrence selected from: =O, =S, $C_1$-$C_4$-alkyl, $C_1$-$C_4$-haloalkyl, halogen, nitro, $OR^{10}$, $SR^{10}$, $S(O)_2R^{10}$, $S(O)_2NR^{10}R^{10}$, $S(O)(NR^{10})R^{10}$, $S(O)R^{10}$, $C(O)R^{10}$, $C(O)NR^{10}R^{10}$, $C(O)OR^{10}$, cyano, $C_2$-$C_4$-alkenyl, $C_2$-$C_4$-alkynyl, $C_3$-$C_6$-cycloalkyl, 4- to 6-membered heterocycloalkyl and $NR^{10}R^{11}$;

$R^{10}$ is independently at each occurrence selected from: H and $C_1$-$C_4$-alkyl;

$R^{11}$ is independently at each occurrence selected from; H, $C_1$-$C_4$-alkyl, C(O)—$C_1$-$C_4$-alkyl and $S(O)_2$—$C_1$-$C_4$-alkyl;

p is an integer independently selected from 0, 1, 2 and 3;

wherein any $R^2$, $R^3$, $R^4$, $R^7$, $R^{10}$, $R^{11}$ or $R^{12}$ group that is alkyl, cycloalkyl, or heterocycloalkyl is optionally substituted, where chemically possible, by 1 to 4 substituents which are each independently selected at each occurrence from the group consisting of: =O; =$NR^a$; =$NOR^a$, $C_1$-$C_4$-alkyl, halo, nitro, cyano, $C_1$-$C_4$-haloalkyl, $C_2$-$C_4$-alkenyl, $C_2$-$C_4$-alkynyl, $NR^aR^b$, $S(O)_2R^a$, $S(O)R^a$, $S(O)(NR^a)R^a$, $S(O)_2NR^aR^a$, $CO_2R^a$, $C(O)R^a$, $CONR^aR^a$ and $OR^a$;

wherein $R^a$ is independently selected from H and $C_1$-$C_4$-alkyl; and $R^b$ is independently H, $C_1$-$C_4$-alkyl, C(O)—$C_1$-$C_4$-alkyl, $S(O)_2$—$C_1$-$C_4$-alkyl;

or an agronomically acceptable salt or N-oxide thereof.

2. A compound of paragraph 1, wherein $R^1$ has the structure

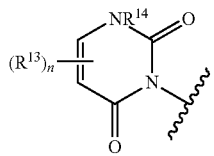

wherein $R^{13}$ is independently at each occurrence selected from $C_1$-$C_4$-alkyl, $C_1$-$C_4$-haloalkyl, halogen, nitro, $OR^{10}$, $SR^{10}$, cyano, $C_2$-$C_4$-alkenyl, $C_2$-$C_4$-alkynyl, $C_3$-$C_6$-cycloalkyl and $NR^{10}R^{11}$;
$R^{14}$ is independently selected from H and $C_1$-$C_4$-alkyl; and n is an integer independently selected from 0, 1 and 2.
3. A compound of paragraph 1, wherein $R^1$ has the structure:

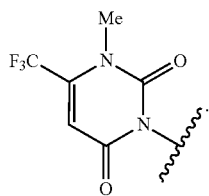

4. A compound of any preceding paragraph wherein $R^3$ is H.
5. A compound of any preceding paragraph wherein $R^4$ is H.
6. A compound of any one of paragraphs 1 to 4, wherein $R^4$ is independently selected from fluoro, $C_1$-$C_4$-haloalkyl and $C_1$-$C_4$-alkyl.
7. A compound of any preceding paragraph, wherein $R^5$ and $R^6$ together with the carbon atom to which they are attached form a $C_3$-$C_6$-cycloalkyl group; wherein the cycloalkyl group is optionally substituted with from 1 to 4 $R^{12}$ groups.
8. A compound of paragraph 7, wherein $R^5$ and $R^6$ together with the carbon atom to which they are attached form a cyclopropyl group; wherein the cyclopropyl group is optionally substituted with from 1 to 4 $R^{12}$ groups.
9. A compound of paragraph 7, wherein $R^5$ and $R^6$ together with the carbon atom to which they are attached form a cyclobutyl group; wherein the cyclobutyl group is optionally substituted with from 1 to 4 $R^{12}$ groups.
10. A compound of paragraph 7, wherein $R^5$ and $R^6$ together with the carbon atom to which they are attached form a cyclopentyl group; wherein the cyclopentyl group is optionally substituted with from 1 to 4 $R^{12}$ groups.
11. A compound of paragraph 7, wherein $R^5$ and $R^6$ may together with the carbon atom to which they are attached form a cyclohexyl group; wherein the cyclohexyl group is optionally substituted with from 1 to 4 $R^{12}$ groups.
12. A compound of paragraph 7, wherein $R^5$ and $R^6$ together with the carbon to which they are attached have the structure:

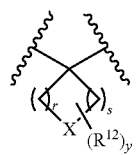

X is selected from: $NR^{15}$, O or $S(=O)_z$; $R^{15}$ is independently selected from H, $C_1$-$C_4$-alkyl, —C(O)—$C_1$-$C_4$-alkyl and —S(O)$_2$—$C_1$-$C_4$-alkyl; z is 0, 1 or 2; y is an integer selected from 0, 1, 2 and 3; r and s are each an integer selected from 0, 1, 2, 3 and 4; and wherein the sum of r and s is 2, 3 or 4.
13. A compound of paragraph 12, wherein r is 1 and s is 1.
14. A compound of paragraph 12, wherein r is 0 and s is 2.
15. A compound of paragraph 12, wherein r is 1 and s is 2.
16. A compound of paragraph 12, wherein r is 0 and s is 3.
17. A compound of paragraph 12, wherein r is 2 and s is 2.
18. A compound of paragraph 12, wherein r is 1 and s is 3.
19. A compound of paragraph 12, wherein r is 0 and s is 4.
20. A compound of any one of paragraphs 12 to 19, wherein X is $NR^{15}$.
21. A compound of any one of paragraphs 12 to 19, wherein X is O.
22. A compound of any one of paragraphs 12 to 19, wherein X is S.
23. A compound of any one of paragraphs 12 to 19, wherein X is $SO_2$.
24. A compound of any one of claims 12 to 23, wherein y is 0.
26. A method for controlling the weeds, the method comprising applying an agronomically effective and substantially non-phytotoxic (to the crop plant) quantity of a compound of any one of paragraphs 1 to 24 to the plants themselves or to the area where it is intended that the plants will grow.
27. A herbicidal composition comprising an effective amount of an active compound of any one of paragraphs 1 to 24.

The term $C_m$-$C_n$ refers to a group with m to n carbon atoms.

The term "alkyl" refers to a monovalent linear or branched saturated hydrocarbon chain. For example, $C_1$-$C_6$-alkyl may refer to methyl, ethyl, n-propyl, iso-propyl, n-butyl, sec-butyl, tert-butyl, n-pentyl and n-hexyl. Any $C_1$-$C_6$-alkyl group may be a $C_1$-$C_4$-alkyl group. The alkyl groups may be unsubstituted.

The term "haloalkyl" refers to a hydrocarbon chain substituted with at least one halogen atom independently chosen at each occurrence from: fluorine, chlorine, bromine and iodine. The halogen atom may be present at any position on the hydrocarbon chain. For example, $C_1$-$C_6$-haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl. Any $C_1$-$C_6$-haloalkyl group may be a $C_1$-$C_4$-haloalkyl group. A haloalkyl group may be a fluoroalkyl group, i.e. a hydrocarbon chain substituted with at least one fluorine atom. Thus, a haloalkyl group may have any amount of halogen substituents. The group may contain a single halogen substituent, it may have two or three halogen substituents, or it may be saturated with halogen substituents.

The term "alkenyl" refers to a branched or linear hydrocarbon chain containing at least one double bond. The double bond(s) may be present as the E or Z isomer. The double bond may be at any possible position of the hydrocarbon chain. For example, "$C_2$-$C_6$-alkenyl" may refer to ethenyl, propenyl, butenyl, butadienyl, pentenyl, pentadienyl, hexenyl and hexadienyl. Any $C_1$-$C_6$-alkenyl group may be a $C_2$-$C_4$-alkenyl group. The alkenyl groups may be unsubstituted.

The term "alkynyl" refers to a branched or linear hydrocarbon chain containing at least one triple bond. The triple bond may be at any possible position of the hydrocarbon chain. For example, "$C_2$-$C_6$-alkynyl" may refer to ethynyl, propynyl, butynyl, pentynyl and hexynyl. Any $C_2$-$C_6$-alkynyl group may be a $C_2$-$C_4$-alkynyl group. The alkynyl groups may be unsubstituted.

The term "cycloalkyl" refers to a saturated hydrocarbon ring system containing 3, 4, 5 or 6 carbon atoms. For example, "$C_3$-$C_6$-cycloalkyl" may refer to cyclopropyl, cyclobutyl, cyclopentyl, cyclohexyl. The cycloalkyl groups may be unsubstituted.

The term y- to z-membered heterocycloalkyl group may refer to a monocyclic or bicyclic saturated or partially saturated group having from y to z atoms in the ring system and comprising 1 or 2 heteroatoms independently selected from O, S and N in the ring system (in other words 1 or 2 of the atoms forming the ring system are selected from O, S and N). By partially saturated it is meant that the ring may comprise one or two double bonds. This applies particularly to monocyclic rings with from 5 to 6 members. The double bond will typically be between two carbon atoms but may be between a carbon atom and a nitrogen atom. The term y- to z-membered heterocycloalkyl group may refer to a monocyclic or bicyclic saturated group having from y to z atoms in the ring system. Examples of heterocycloalkyl groups include; piperidine, piperazine, morpholine, thiomorpholine, pyrrolidine, tetrahydrofuran, tetrahydrothiophene, dihydrofuran, tetrahydropyran, dihydropyran, dioxane, azepine. A heterocycloalkyl group may be unsubstituted.

Aryl groups may be any aromatic carbocyclic ring system (i.e. a ring system containing $2(2n+1)\pi$ electrons). Aryl groups may have from 6 to 12 carbon atoms in the ring system. Aryl groups will typically be phenyl groups. Aryl groups may be naphthyl groups or biphenyl groups.

In any of the above aspects and embodiments, heteroaryl groups may be any aromatic (i.e. a ring system containing $2(2n+1)\pi$ electrons or n electrons that can overlap with the $\pi$ system) 5 or 6 membered ring system comprising from 1 to 4 heteroatoms independently selected from O, S and N (in other words from 1 to 4 of the atoms forming the ring system are selected from O, S and N). Thus, any heteroaryl groups may be independently selected from: 5 membered heteroaryl groups in which the heteroaromatic ring is substituted with 1-4 heteroatoms independently selected from O, S and N; and 6-membered heteroaryl groups in which the heteroaromatic ring is substituted with 1-3 (e.g. 1-2) nitrogen atoms. Specifically, heteroaryl groups may be independently selected from: pyrrole, furan, thiophene, pyrazole, imidazole, oxazole, isoxazole, triazole, oxadiazole, thiadiazole, tetrazole; pyridine, pyridazine, pyrimidine, pyrazine, triazine.

Compounds of the invention containing one or more asymmetric carbon atoms can exist as two or more stereoisomers. Where a compound of the invention contains a double bond such as a C═C or C═N group, geometric cis/trans (or Z/E) isomers are possible. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of the invention, including compounds exhibiting more than one type of isomerism, and mixtures of one or more thereof. Also included are acid addition or base salts wherein the counter ion is optically active, for example, d-lactate or l-lysine, or racemic, for example, dl-tartrate or dl-arginine.

The compounds of the invention may be obtained, stored and/or used in the form of an agronomically acceptable salt. Suitable salts include, but are not limited to, salts of acceptable inorganic acids such as hydrochloric, sulfuric, phosphoric, nitric, carbonic, boric, sulfamic, and hydrobromic acids, or salts of agronomically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulfonic, toluenesulfonic, benzenesulfonic, salicylic, sulfanilic, aspartic, glutamic, edetic, stearic, palmitic, oleic, lauric, pantothenic, tannic, ascorbic and valeric acids. Suitable salts also include salts of inorganic and organic bases, e.g. counterions such as Na, Ca, K, Li, Mg, ammonium, trimethylsulfonium. The compounds may also be obtained, stored and/or used in the form of an N-oxide.

Cis/trans isomers may be separated by conventional techniques well known to those skilled in the art, for example, chromatography and fractional crystallisation.

Conventional techniques for the preparation/isolation of individual enantiomers when necessary include chiral synthesis from a suitable optically pure precursor or resolution of the racemate (or the racemate of a salt or derivative) using, for example, chiral high performance liquid chromatography (HPLC). Thus, chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and for specific examples, 0 to 5% by volume of an alkylamine e.g. 0.1% diethylamine. Concentration of the eluate affords the enriched mixture.

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, "Stereochemistry of Organic Compounds" by E. L. Eliel and S. H. Wilen (Wiley, 1994).

The activity of the compounds of the present invention can be assessed by a variety of in silico, in vitro and in vivo assays. In silico analysis of a variety of compounds has been demonstrated to be predictive of ultimate in vitro and even in vivo activity.

The present invention also includes all environmentally acceptable isotopically-labelled compounds of formulae I to VIII and their syntheses, wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Isotopically-labelled compounds can generally be prepared by conventional techniques known to those skilled in the art or by processes analogous to those described using an appropriate isotopically-labelled reagent in place of the non-labelled reagent previously employed.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

If appropriate, the compounds of the invention can, at certain concentrations or application rates, be used as herbicides.

According to another aspect of the present invention, there is provided a method for controlling the weeds, the method comprising applying an agronomically effective and substantially non-phytotoxic (to the crop plant) quantity of a compound according to the invention to the plants themselves or to the area where it is intended that the plants will grow.

The pesticide may be applied as a foliar application, stem application, drench or drip application (chemigation) to the plant or to the fruit of the plant or to soil or to inert substrate (e.g. inorganic substrates like sand, rockwool, glasswool; expanded minerals like perlite, vermiculite, zeolite or expanded clay), Pumbe, Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics).

In a further aspect, the present invention also relates to a herbicidal composition comprising an effective amount of an active compound of the invention. The composition may further comprise one or more additional herbicides.

The term "effective and non-phytotoxic amount" means an amount of pesticide according to the invention which is sufficient to control or destroy any of the targeted pests present or liable to appear in the crops and which does not have any significant detrimental effect on the crops or indeed has a positive effect on plant vigour and yield in the absence of target organism. The amount will vary depending on the pest to be controlled, the type of crop, the climatic conditions and the compounds included in the pesticidal composition. This amount can be determined by systematic field trials, which are within the capabilities of a person skilled in the art.

Depending on their particular physical and/or chemical properties, the active compounds of the invention can be formulated as solutions, emulsions, suspensions, powders, foams, pastes, granules, aerosols, microencapsulations in polymeric substances and also as ULV cold and warm fogging formulations.

The active compounds can be used neat, or in the form of a formulation, e.g. ready-to-use solutions, emulsions, water- or oil-based suspensions, powders, wettable powders, pastes, soluble powders, dusts, soluble granules, granules for broadcasting, suspoemulsion concentrates, natural substances impregnated with active compound, synthetic substances impregnated with active compound, fertilizers and also microencapsulations in polymeric substances. Application may be carried out, for example, by watering, spraying, atomizing, broadcasting, dusting, foaming, spreading, etc. It is also possible to apply the active compounds by the ultra-low volume method or to inject the preparation of active compound or the active compound itself into the soil.

Formulations containing the compounds of the invention are produced in a known manner, for example by mixing the compounds with extenders (e.g. liquid solvents and/or solid carriers), optionally with the use of surfactants (e.g. emulsifiers and/or dispersants and/or foam-formers).

The formulations are prepared either in factories/production plants or alternatively before or during the application.

Auxiliaries are substances which are suitable for imparting to the composition itself and/or to preparations derived therefrom (for example spray liquors) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to use, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and also their ethers and esters, ketones such as acetone, methyl ethyl ketone, methyl isobutyl ketone or cyclohexanone, strongly polar solvents such as dimethylformamide and dimethyl sulfoxide.

Suitable solid carriers are: for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat- and/or POP-POE adducts, POE- and/or POP-polyol derivatives, POE- and/or POP-sorbitan- or -sugar adducts, alkyl or aryl sulfates, alkyl- or arylsulfonates and alkyl or aryl phosphates or the corresponding PO-ether adducts.

Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulfonic acid derivatives, unmodified and modified celluloses, aromatic and/or aliphatic sulfonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

Further additives may be mineral and vegetable oils. It is also possible to add colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils and waxes.

The formulations may also comprise stabilizers, e.g. low-temperature stabilizers, preservatives, antioxidants, light stabilizers or other agents which improve chemical and/or physical stability.

The formulations generally comprise between 0.01 and 98% by weight of active compound, preferably between 0.1 and 95% and particularly preferably between 0.5 and 90%.

The active compounds according to the invention can also be used as a mixture with other known herbicides for example, to improve the activity spectrum or to reduce or slow the development of resistance.

A mixture with other known active compounds such as nematicides, acaricides, fungicides, insecticides or bactericides, or with fertilizers and growth regulators, safeners or semiochemicals is also possible.

Exemplary application rates of the active compounds according to the invention are: when treating leaves: from 0.1 to 10 000 g/ha, preferably from 10 to 1000 g/ha, particularly preferably from 50 to 300 g/ha (when the application is carried out by watering or dripping, it is even possible to reduce the application rate, especially when inert substrates such as rock wool or perlite are used); when treating the soil: from 0.1 to 10 000 g/ha, preferably from 1 to 5000 g/ha.

A formulation which could be used to administer the compounds, particularly in the context of testing for activity, would be to supply all compounds as a 10% solution in DMSO. If there are solubility problems this can be helped by adding acetone (e.g. to dilute a DMSO solution/suspension by 50% resulting in a 5% solution of the compound in DMSO/acetone. The administration formulation is then obtained by adding the DMSO (or DMSO/acetone) solution to a 0.1% solution of Tween 20™ in water to give the required concentration. The result is likely to be an emulsion that can be sprayed. If crystallisation occurs, resulting in inconsistent results, further DMSO can be added to the test solution.

The compositions according to the invention are suitable for protecting any plant variety which is employed in agriculture, in the greenhouse, in forests or in horticulture and, in particular, cereals (e.g. wheat, barley, rye, millet and oats), maize, cotton, soya beans, rice, potatoes, sunflowers, beans, coffee, beet (for example sugar beet and fodder beet), peanuts, vegetables (e.g. tomatoes, cucumbers, onions and lettuce), lawns, fruit and nut trees (e.g. apples pears peaches nectarines, apricots, hazelnut, pecan, macadamia, pistachio), soft fruit (e.g. strawberries, raspberries, blackcurrants, redcurrants), grapevines, bananas, cocoa and ornamental plants.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular nematodes, which are encountered in agriculture, in horticulture, in animal husbandry, in forests, in gardens and leisure facilities, in the protection of stored products and of materials, and in the hygiene sector. They may be preferably employed as crop protection agents.

Use as Herbicides

Some compounds of the invention may also have herbicidal activity against a broad spectrum of economically important mono- and dicotyledonous harmful plants. Some compounds of the invention may have herbicidal activity against monocotyledonous plants but no activity or little activity against dicotyledonous crops. Other compounds of the invention may be selective, having excellent herbicidal activity against dicotyledonous plants but no activity or little activity against monocotyledonous crops.

Difficult-to-control perennial weeds which produce shoots from rhizomes, root stocks or other perennial organs may also be controlled by herbicidal compounds. Here, the substances can be applied by the pre-sowing method, the pre-emergence method and/or the post-emergence method.

The following are illustrative examples of monocotyledonous weeds that may be controlled by herbicidal compounds: *Avena* spp., *Alopecurus* spp., *Brachiaria* spp., *Digitaria* spp., *Lolium* spp., *Echinochloa* spp., *Panicum* spp., *Phalaris* spp., Poa spp., *Setaria* spp. and also *Bromus* spp. such as *Bromus catharticus, Bromus secalinus, Bromus erectus, Bromus tectorum* and *Bromus japonicus* and *Cyperus* species from the annual group, and, *Agropyron, Cynodon, Imperata* and Sorghum and also perennial *Cyperus* species, from the perrenial group.

The following are illustrative examples of dicotyledonous weeds that may be controlled by herbicidal compounds: *Abutilon* spp., *Amaranthus* spp., *Chenopodium* spp., *Chrysanthemum* spp., *Galium* spp. such as *Galium aparine, Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. and *Viola* spp., *Xanthium* spp., in the case of annuals, and *Convolvulus, Cirsium, Rumex* and *Artemisia* in the case of the perennials.

If herbicidal compounds are applied to the soil surface before or during germination, the weed seedlings are inhibited or prevented completely from emerging or else the weeds grow until they have reached the cotyledon stage, but then their growth stops, and, eventually, they die completely.

If herbicidal compounds are applied post-emergence to the green parts of the plants, growth typically stops following the treatment, and the weed plants remain substantially at the growth stage of the point of time of application, or they die completely, so that in this manner competition from the weeds is eliminated quickly and in a sustained manner.

DETAILED DESCRIPTION—SYNTHESIS

The skilled person will appreciate that adaptation of methods known in the art could be applied in the manufacture of the compounds of the present invention.

For example, the skilled person will be immediately familiar with standard textbooks such as "Comprehensive Organic Transformations—A Guide to Functional Group Transformations", RC Larock, Wiley-VCH (1999 or later editions); "March's Advanced Organic Chemistry—Reactions, Mechanisms and Structure", MB Smith, J. March, Wiley, (5th edition or later); "Advanced Organic Chemistry, Part B, Reactions and Synthesis", F A Carey, R J Sundberg, Kluwer Academic/Plenum Publications, (2001 or later editions); "Organic Synthesis—The Disconnection Approach", S Warren (Wiley), (1982 or later editions); "Designing Organic Syntheses" S Warren (Wiley) (1983 or later editions); "Heterocyclic Chemistry", J. Joule (Wiley 2010 edition or later); ("Guidebook To Organic Synthesis" RK Mackie and DM Smith (Longman) (1982 or later editions), etc., and the references therein as a guide.

The skilled person is familiar with a range of strategies for synthesising organic and particularly heterocyclic molecules and these represent common general knowledge as set out in text books such as Warren "Organic Synthesis: The Disconnection Approach"; Mackie and Smith "Guidebook to Organic Chemistry"; and Clayden, Greeves, Warren and Wothers "Organic Chemistry".

The skilled chemist will exercise his or her judgement and skill as to the most efficient sequence of reactions for synthesis of a given target compound and will employ protecting groups as necessary.

This will depend inter alia on factors such as the nature of other functional groups present in a particular substrate. Clearly, the type of chemistry involved will influence the choice of reagent that is used in the synthetic steps, the need, and type, of protecting groups that are employed, and the sequence for accomplishing the protection/deprotection steps. These and other reaction parameters will be evident to the skilled person by reference to standard textbooks and to the examples provided herein.

Sensitive functional groups may need to be protected and deprotected during synthesis of a compound of the invention. This may be achieved by conventional methods, for example as described in "Protective Groups in Organic Synthesis" by TW Greene and PGM Wuts, John Wiley & Sons Inc (1999), and references therein.

Throughout this specification these abbreviations have the following meanings:
Boc—tert-butyloxycarbonyl DCM—dichloromethane
DMF—N,N-dimethylformamide DIPEA—diisopropylethylamine
DMAP—N,N-dimethylaminopyridine DMSO—dimethylsulfoxide
HATU—(1-[bis(dimethylamino)methylene]-1H-1,2,3-triazolo[4,5-b]pyridinium-3-oxide hexafluorophosphate) $Et_2O$—Diethyl ether
IPA—isopropyl alcohol EtOAc—Ethyl acetate
PE—petroleum ether THF—tetrahydrofuran
TFA—trifluoroacetic acid MeOH—methanol
HPLC—high performance liquid chromatography r.t.—room temperature Certain compounds of the invention can be made according to the following general synthetic schemes. Certain compounds of the invention can be made according to or analogously to the methods described in Examples 1 to 14.

General Synthetic Schemes

Scheme A describes a general approach to certain compounds of the invention. Compounds of formula A can be reacted with N,N-dimethylchloroformamide (e.g. by deprotonating with NaH and reacting in DMF) to provide compounds of formula B. Treatment under ring closing conditions (e.g. with $POCl_3$ and $PCl_5$) can provide compounds of formula C. Reaction with amino acid D (e.g. in acetic acid at 90° C.) can provide compounds of formula E. Alkylation (where $R^{14}$ is Me, this can be achieved with methyl iodide and potassium carbonate in DMF at 60° C.) can provide ester F which, on ester cleavage (where $R^{14}$ is Me this can be achieved using $BBr_3$ in DCM), can be converted to acid G. Acid G can be coupled with sulfonamide H to provide compounds of formula J, a subset of compounds of the invention. This can be achieved either by converting the acid to the acid chloride (e.g. using $(COCl)_2$ and DMF) and reacted with the sulfonamide H in the presence of a base (e.g. triethylamine in DCM in the presence of DMAP) or by using a suitable coupling system (e.g. HATU and DIPEA in DCM).

Scheme A

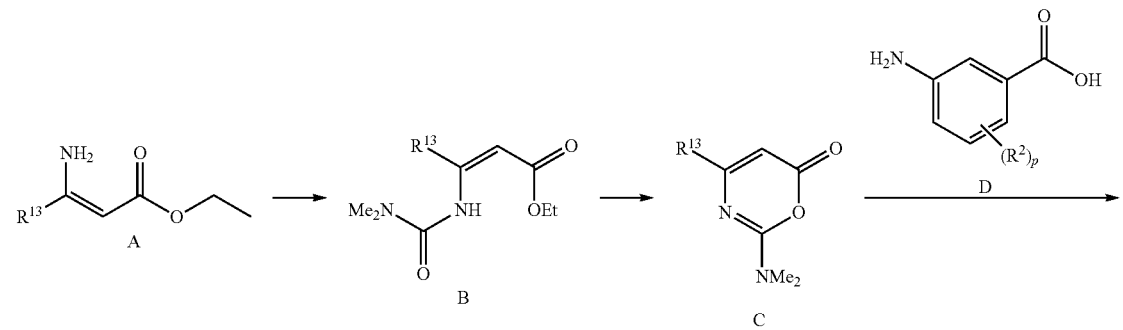

-continued

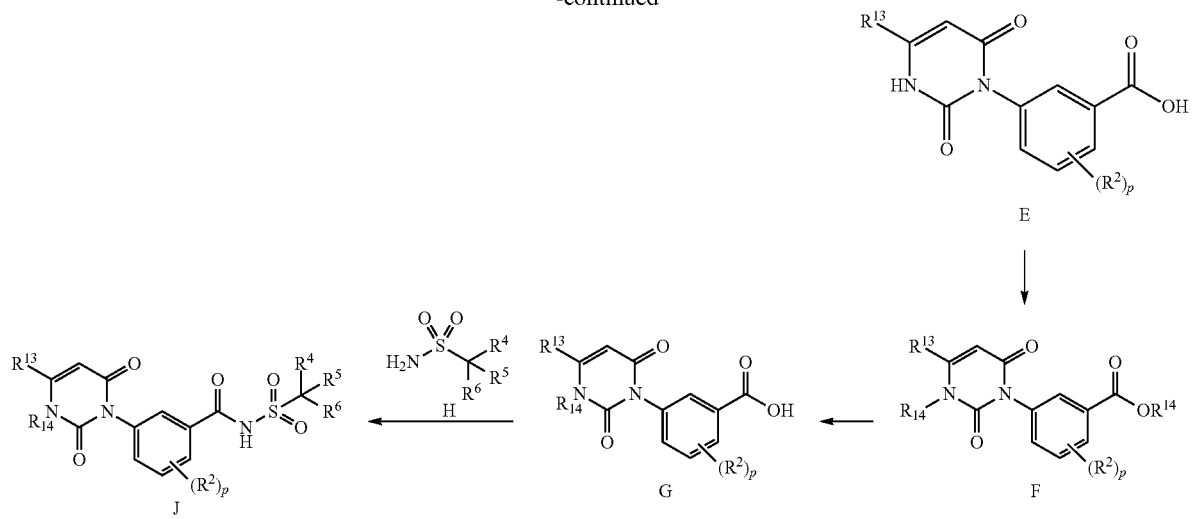

Certain aminoacids of formula D can be made according to scheme B. A benzoic ester K can be nitrated at the meta position (e.g. using nitric acid and sulfuric acid) to form benzoic ester L. Reduction of the nitro group (e.g. using iron in the presence of ammonium chloride in methanol and water at 90° C.) followed by ester cleavage (e.g. using NaOH in ethanol) can provide aminoacid D.

Scheme B

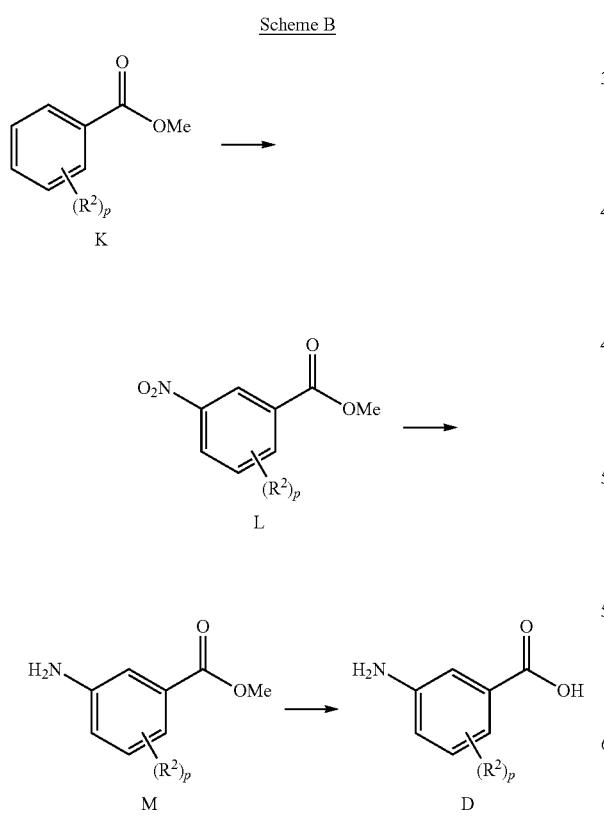

Sulfonamides of formula H can be made from the corresponding sulfonyl chloride N, e.g. by reacting with ammonium hydroxide in THF (Scheme C).

Scheme C

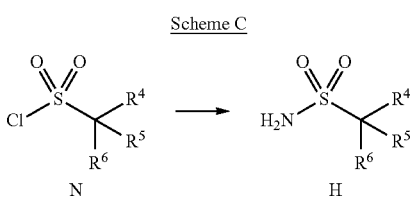

General Methods

Flash chromatography was carried out using a Biotage Isolera 4, with Biotage® SNAP KP-Sil cartridges, packed with 50 μm silica particles with a surface area of 500 m²/g, or alternative cartridges (e.g. Puriflash, produced by Interchim) where stated, or using silica gel (40-63 μm particles). Visualisation was carried out with UV light (254 nm) and by staining with either potassium permanganate, phosphomolybdic acid (PMA) or ninhydrin solutions.

All $^1$H NMR spectra were obtained on a Bruker AVIII 400 with 5 mm QNP or Bruker AVI 500 with 5 mm QNP. Chemical shifts are expressed in parts per million (δ) and are referenced to the solvent. Coupling constants J are expressed in Hertz (Hz).

ESI-MS data were obtained using a Waters Acquity H-Class UPLC. (Column: CSH C18 2.1×50 mm 1.7 μm @ 50 C, Solvents: A-Water B-Acetonitrile+0.1% Formic Acid or Solvents: A-Water B-Acetonitrile+0.1% by volume of 28% (by weight) aqueous ammonia solution, Gradient: 0.2-2.5 mins 2-98% B 2.5-3.0 mins 98% B, Flow rate: 1.0 mL/min.) Data for product ions alone are reported.

MS was carried out on a Waters Alliance ZQ MS, using a LC column as described below under Method C, D and F. Wavelengths were 254 and 210 nM.

Method C (5 Minute Acidic pH)

Column: YMC-Triart C18 50×2 mm, 5 μm. Flow rate: 0.8 mL/min. Injection volume: 5 μL.

| Mobile Phase | A | H₂O | | |
|---|---|---|---|---|
| | B | CH₃CN | | |
| | C | 50% H₂O/50% CH₃CN + 1.0% formic acid | | |
| Time (min) | A (%) | B (%) | C (%) | |
| 0 | 95 | 0 | 5 | |
| 4 | 0 | 95 | 5 | |
| 4.4 | 0 | 95 | 5 | |
| 4.5 | 95 | 5 | 0 | |
| 4.5 | | STOP | | |

Method D (15 Minute Acidic pH)
Column YMC Triart-C18 50×2 mm, 5 μm Flow rate: 0.8 mL/min. Injection volume: 10 μL

| Mobile Phase | A | H₂O | | |
|---|---|---|---|---|
| | B | CH₃CN | | |
| | C | 50% H₂O/50% CH₃CN + 1.0% formic acid | | |
| Time (min) | A (%) | B (%) | C (%) | |
| 0 | 95 | 0 | 5 | |
| 2.0 | 95 | 0 | 5 | |
| 12.0 | 0 | 95 | 5 | |
| 14.0 | 0 | 95 | 5 | |
| 14.2 | 95 | 0 | 5 | |

Method F (3.5 Minute Acidic pH)
Mobile phases: Water (A)/Acetonitrile (B) both with 0.1% (v/v) Formic Acid

| Time | % A | % B | Flow rate (mL/min) |
|---|---|---|---|
| Initial | 98 | 2 | 1.0 |
| 0.2 | 98 | 2 | 1.0 |
| 2.5 | 2 | 98 | 1.0 |
| 3.0 | 2 | 98 | 1.0 |
| 3.1 | 98 | 2 | 1.0 |
| 3.5 | 98 | 2 | 1.0 |

Column: CSH C18 2.1×50 mm, 1.7 μm @ 50° C.
All reagents were obtained from commercial suppliers and used as supplied unless otherwise stated.
All examples are named using ChemBioDraw Ultra 14.0.

Example 1: 2-Chloro-4-fluoro-5-(3-methyl-2,6-di-oxo-4-(trifluoromethyl)-3,6-dihydropyrimidin-1(2H)-yl)-N-((tetrahydro-2H-pyran-4-yl)sulfonyl)benzamide

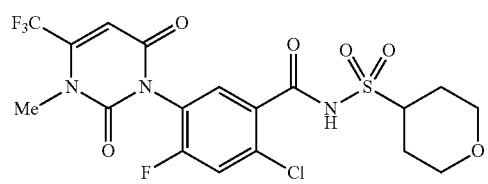

2-Chloro-4-fluoro-5-[3-methyl-2,6-dioxo-4-(trifluoromethyl)pyrimidin-1-yl]benzoic acid (Intermediate A) was prepared according to the procedure provided in US 2004/0018942. To a solution of Intermediate A (100.0 mg, 0.27 mmol) in dichloromethane (3.5 mL) was added DMF (5 drops). Oxalyl chloride (0.07 mL, 0.81 mmol) was then added dropwise to the reaction and it was stirred at r.t. for 1.5 h. The reaction mixture was then concentrated in vacuo. Toluene (2 mL) was then added to the crude acyl chloride concentrate and the flask was purged with nitrogen. A solution of tetrahydro-2H-pyran-4-sulfonamide (45.1 mg, 0.27 mmol), DMAP (1.7 mg, 0.01 mmol) and triethylamine (0.13 mL, 0.96 mmol) was prepared in toluene (1 mL) and was added to the pre-prepared acyl chloride solution and heated to 55° C. for 18 h. The reaction mixture was added to a stirred flask containing ice water. EtOAc (10 mL) and sat. brine (10 mL) were then added to the resultant biphasic mixture. The aqueous layer was re-extracted with EtOAc (3×5 mL) and the combined organics were then dried with Na₂SO₄ and concentrated in vacuo. The residue was purified by flash chromatography (SiO₂, 25-100% EtOAc (0.1% AcOH) in PE (0.1% AcOH)) to afford the title compound as a brown solid (18.5 mg, 13%). ¹H NMR δ$_H$(CDCl₃, 500 MHz) 8.02 (s, 1H), 7.96 (d, J=8.1 Hz, 1H), 7.31 (d, J=9.4 Hz, 1H), 6.35 (s, 2H), 4.08 (dd, J=11.0, 4.2 Hz, 2H), 3.55 (d, J=1.0 Hz, 3H), 3.38 (td, J=12.1, 2.2 Hz, 2H), 3.08 (t, J=3.7 Hz, 1H), 2.06-2.00 (m, 2H), 1.85 (ddd, J=25.5, 12.2, 4.7 Hz, 2H). LCMS (Method D): 6.62 min (513.0, [M+H]⁺)

Intermediate B: tert-Butyl 4-sulfamoylpiperidine-1-carboxylate

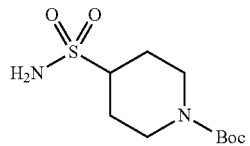

To a solution of 1-boc-4-chlorosulfonylpiperidine (1.0 g, 3.52 mmol) in THF (22 mL) at 00° C. was added ammonium hydroxide (4.90 ml, 35.20 mmol) in a dropwise manner. The reaction was allowed to proceed for 3 h at r.t. The reaction mixture was concentrated under reduced pressure to afford a white solid. To the crude residue was added 20 mL water and 20 mL EtOAc and the layers separated. The aqueous layer was then re-extracted with 3×10 mL EtOAc and the combined organics were dried with Na₂SO₄ and concentrated under reduced pressure to afford the title compound as a white solid (879.3 mg, 94%). ¹H NMR δ$_H$ (CDCl₃, 500 MHz) δ 4.40 (s, 2H), 4.29 (s, 2H), 3.06 (tt, J=12.0, 3.6 Hz, 1H), 2.74 (t, J=13.0 Hz, 2H), 2.17 (t, J=6.6 Hz, 2H), 1.72 (qd, J=12.5, 4.6 Hz, 2H), 1.46 (s, 9H).

Intermediate C: tert-Butyl 4-(N-(2-chloro-4-fluoro-5-(3-methyl-2,6-dioxo-4-(trifluoromethyl)-3,6-dihydropyrimidin-1(2H)-yl)benzoyl)sulfamoyl)piperidine-1-carboxylate

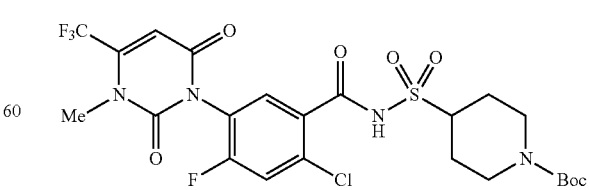

Prepared according to the procedure described in Example 1 using Intermediate A (200.0 mg, 0.55 mmol, oxalyl chloride (0.14 mL, 1.64 mmol), Intermediate B (144.0 mg, 0.55 mmol), 4-(dimethylamino)pyridine (3.3 mg, 0.03 mmol) and triethylamine (0.27 mL, 1.91 mmol) to afford the title compound as a tan solid (250.0 mg, 75%). $^1$H NMR $\delta_H$ (CDCl$_3$, 500 MHz) 8.95 (s, 1H), 7.78 (d, J=7.4 Hz, 1H), 7.41 (d, J=8.9 Hz, 1H), 6.38 (s, 1H), 4.28 (s, 2H), 3.90-3.76 (m, 1H), 3.57 (s, 3H), 2.78 (s, 1H), 1.86 (ddd, J=25.1, 12.5, 4.6 Hz, 2H), 1.25 (t, J=3.5 Hz, 2H). LCMS (Method C): 3.03 min (611.3, [M−H]$^-$).

Example 2: 2-Chloro-4-fluoro-5-(3-methyl-2,6-dioxo-4-(trifluoromethyl)-3,6-dihydropyrimidin-1(2H)-yl)-N-(piperidin-4-ylsulfonyl)benzamide hydrochloride

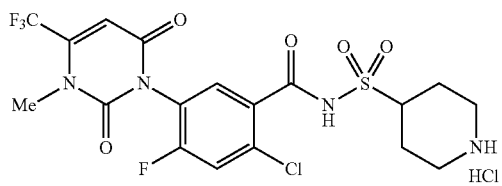

2

To a solution of Intermediate C (70.0 mg, 0.11 mmol) in dioxane (1.4 mL), HCl (1.4 mL, 5.6 mmol, 4 M in dioxane) was added. The reaction was allowed to proceed for 3 hours at r.t. The reaction mixture was concentrated under reduced pressure and the resultant yellow solid was suspended in diethyl ether and filtered off, washing with diethyl ether (10 mL) to afford the title compound as a yellow powder (42.1 mg, 67%). $^1$H NMR $\delta_H$ (MeOD-d$_4$, 500 MHz) 7.76 (d, J=7.4 Hz, 1H), 7.65 (d, J=9.4 Hz, 1H), 6.49 (s, 1H), 4.02 (t, J=11.4 Hz, 1H), 3.65-3.45 (m, 6H), 3.25-3.11 (m, 3H), 2.46 (d, J=13.6 Hz, 2H), 2.16 (td, J=15.5, 4.1 Hz, 2H). LCMS (Method D): 5.30 min (513.0, [M+H]$^+$).

Example 3: 2-Chloro-4-fluoro-5-(3-methyl-2,6-dioxo-4-(trifluoromethyl)-3,6-dihydropyrimidin-1(2H)-yl)-N-((1-methylpiperidin-4-yl)sulfonyl)benzamide hydrochloride

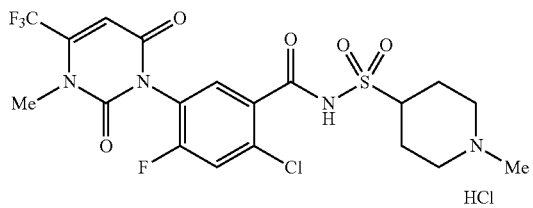

3

To a solution of Intermediate C (55.0 mg, 0.09 mmol), formic acid (179 μl) and formaldehyde (37% in water, 67 μl, 0.9 mmol) were added. The reaction was then sealed and heated to 100° C. for 2 h. The reaction mixture was concentrated under reduced pressure and to the resultant brown solid was added HCl (1 mL, 4 M in dioxane) and the reaction was stirred for 1 h at r.t. The reaction mixture was then concentrated under reduced pressure and the resultant off-white solid was suspended in diethyl ether and filtered, washing with diethyl ether (10 mL) to afford the title compound as an off white powder (12.8 mg, 25%). $^1$H NMR $\delta_H$ (MeOD-d$_4$, 500 MHz) 7.76 (d, J=7.2 Hz, 1H), 7.66 (d, J=9.3 Hz, 1H), 6.49 (s, 1H), 4.07-3.93 (m, 1H), 3.72 (d, J=12.7 Hz, 2H), 3.56 (s, 3H), 3.20 (d, J=13.3 Hz, 2H), 2.93 (s, 3H), 2.51 (d, J=12.9 Hz, 2H), 2.26-2.08 (m, 2H). LCMS (Method D): 5.31 min (527.0, [M+H]$^+$).

Intermediate D: tert-Butyl 3-sulfamoylpyrrolidine-1-carboxylate

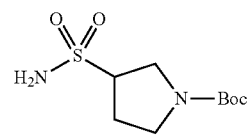

Prepared according to the procedure described in Intermediate B using tert-butyl 3-(chlorosulfonyl)pyrrolidine-1-carboxylate (1.0 g, 3.71 mmol), THF (23.2 ml) and ammonium hydroxide (5.2 ml, 37.1 mmol) to afford the title compound as a colourless solid (744.6 mg, 80%). $^1$H NMR $\delta_H$ (CDCl$_3$, 500 MHz) 4.87 (s, 2H), 3.76 (br. s, 3H), 3.62 (m, 1H), 3.49-3.37 (m, 1H), 2.42-2.25 (m, 2H), 1.46 (s, 9H).

Intermediate E: tert-Butyl 3-(N-(2-chloro-4-fluoro-5-(3-methyl-2,6-dioxo-4-(trifluoromethyl)-3,6-dihydropyrimidin-1(2H)-yl)benzoyl)sulfamoyl)pyrrolidine-1-carboxylate

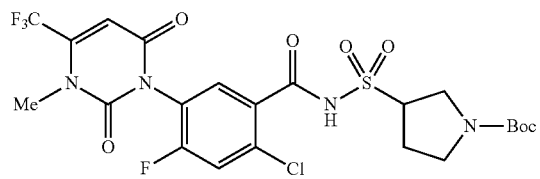 [SMILES: Cn1c(C(F)(F)F)cc(=O)n(-c2cc(C(=O)NS(=O)(=O)C3CCN(C(=O)OC(C)(C)C)C3)c(Cl)cc2F)c1=O]

Prepared according to the procedure described in Example 1 using Intermediate A (200.0 mg, 0.55 mmol), oxalyl chloride (0.14 mL, 1.636 mmol), Intermediate D (137.0 mg, 0.55 mmol), 4-(dimethylamino)pyridine (3.3 mg, 0.03 mmol) and triethylamine (0.27 mL, 1.91 mmol) to afford the title compound as an orange solid (136.7 mg, 42%). $^1$H NMR $\delta_H$ (CDCl$_3$, 500 MHz) 8.04 (d, J=11.2 Hz, 2H), 7.34 (d, J=9.1 Hz, 1H), 6.34 (dd, J=9.1, 5.2 Hz, 1H), 3.95 (dd, J=23.4, 16.3 Hz, 2H), 3.58-3.53 (m, 3H), 3.43-3.32 (m, 2H), 2.55 (s, 1H), 2.42-2.27 (m, 2H), 1.45 (s, 9H). LCMS (Method C): 2.19 min (599.0, [M+H]$^+$).

Example 4: 2-Chloro-4-fluoro-5-(3-methyl-2,6-dioxo-4-(trifluoromethyl)-3,6-dihydropyrimidin-1(2H)-yl)-N-(pyrrolidin-3-ylsulfonyl)benzamide hydrochloride

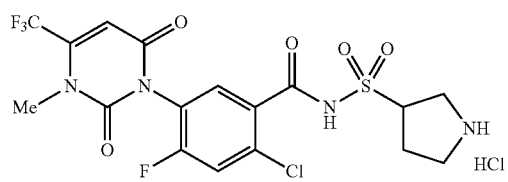

4

Prepared according to the procedure described for Example 2 using Intermediate E (137.6 mg, 0.23 mmol), dioxane (2.8 mL) and HCl (2.8 mL, 11.2 mmol, 4 M in dioxane) to afford the title compound as an orange powder (56.6 mg, 49%). $^1$H NMR $\delta_H$ (MeOD-d$_4$, 500 MHz) 8.12 (d, J=3.6 Hz, 1H), 7.62 (t, J=9.2 Hz, 1H), 7.57-7.47 (m, 1H), 6.47 (s, 1H), 3.99-3.81 (m, 2H), 3.44 (s, 3H), 3.45-3.35 (m, 2H), 2.60-2.30 (m, 4H).

Example 5: 2-Chloro-4-fluoro-5-(3-methyl-2,6-dioxo-4-(trifluoromethyl)-3,6-dihydropyrimidin-1(2H)-yl)-N-((1-methylpyrrolidin-3-yl)sulfonyl)benzamide hydrochloride

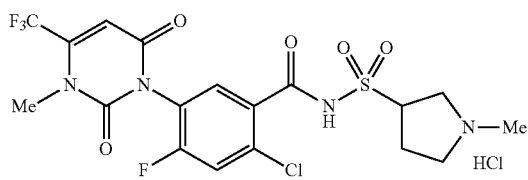

5

Prepared according to the procedure described for Example 3 using Intermediate E (100.0 mg, 0.167 mmol), formic acid (835 µl) and formaldehyde (37% in water, 188 µl, 2.5 mmol) to afford the title compound as an off white powder (54.2 mg, 59%). $^1$H NMR $\delta_H$ (MeOD-d$_4$, 500 MHz) b 7.72 (d, J=7.4 Hz, 1H), 7.64 (d, J=9.4 Hz, 1H), 6.46 (s, 1H), 4.33-4.13 (m, 1H), 3.90-3.55 (m, 4H), 3.53 (s, 3H), 3.03 (t, J=7.6 Hz, 3H), 2.79-2.66 (m, 1H), 2.62-2.52 (m, 1H). LCMS (Method D): 5.32 min (513.1, [M+H]$^+$).

Intermediate F: tert-Butyl 3-sulfamoylazetidine-1-carboxylate

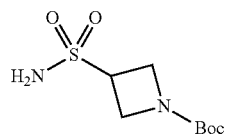

Prepared according to the procedure described in Intermediate B using tert-butyl 3-(chlorosulfonyl)azetidine-1-carboxylate (250.0 mg, 0.98 mmol), THF (3.3 ml) and ammonium hydroxide (1.36 ml, 9.78 mmol) to afford the title compound as a white solid (216.5 mg, 94%). $^1$H NMR $\delta_H$ (CDCl$_3$, 500 MHz) 4.76 (s, 2H), 4.28-4.21 (m, 2H), 4.17 (dd, J=10.1, 5.2 Hz, 2H), 4.00 (ddd, J=8.3, 6.6, 4.2 Hz, 1H), 1.44 (s, 9H).

Intermediate G: tert-Butyl 3-(N-(2-chloro-4-fluoro-5-(3-methyl-2,6-dioxo-4-(trifluoromethyl)-3,6-dihydropyrimidin-1(2H)-yl)benzoyl)sulfamoyl)azetidine-1-carboxylate

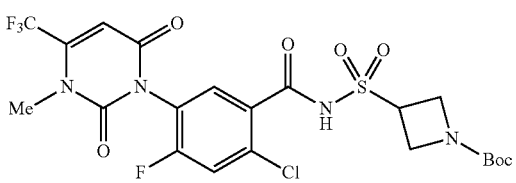 [SMILES: Cn1c(C(F)(F)F)cc(=O)n(-c2cc(C(=O)NS(=O)(=O)C3CN(C(=O)OC(C)(C)C)C3)c(Cl)cc2F)c1=O]

A solution of Intermediate A (200.0 mg, 0.54 mmol), Intermediate F (155.0 mg, 0.65 mmol), HATU (249.0 mg, 0.65 mmol) and N,N-diisopropylethylamine (0.28 mL, 1.64 mmol) was prepared in anhydrous dichloromethane (1.65 mL). The flask was sealed and the reaction was allowed to proceed for 2 hours at r.t. Water (30 mL), HCl (1 M, 1.7 mL) and sat. brine (5 mL) were added to the reaction mixture and the layers separated. The aqueous layer was re-extracted with dichloromethane (3×5 mL) and the combined organics were then dried with Na$_2$SO$_4$ and concentrated under reduced pressure to afford the title compound as an off-white solid (297.2 mg, 93%). $^1$H NMR $\delta_H$ (CDCl$_3$, 500 MHz) 7.78 (d, J=7.4 Hz, 1H), 7.41 (d, J=8.8 Hz, 1H), 6.38 (s, 1H), 4.60 (ddd, J=8.5, 5.7, 3.0 Hz, 1H), 4.42-4.35 (m, 2H), 4.29-4.23 (m, 2H), 3.57 (s, 3H), 1.45 (s, 9H). LCMS (Method C): 2.81 min (583.2, [M−H]$^-$).

Example 6: N-(Azetidin-3-ylsulfonyl)-2-chloro-4-fluoro-5-(3-methyl-2,6-dioxo-4-(trifluoromethyl)-3,6-dihydropyrimidin-1(2H)-yl)benzamide hydrochloride

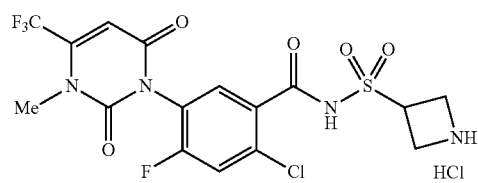

6

Prepared according to the procedure described for Example 2 using Intermediate G (100.0 mg, 0.17 mmol), dioxane (1 mL) and HCl (0.85 mL, 3.4 mmol, 4 M in dioxane) to afford the title compound as a white powder (77.1 mg, 87%). $^1$H NMR $\delta_H$ (MeOD-d$_4$, 500 MHz) 7.71 (d, J=7.4 Hz, 1H), 7.62 (d, J=9.4 Hz, 1H), 6.46 (s, 1H), 4.53-4.49 (m, 4H), 4.29-4.22 (m, 1H), 3.52 (d, J=0.9 Hz, 3H). LCMS (Method D): 5.26 min (484.9, [M+H]$^+$).

Example 7: 2-Chloro-4-fluoro-5-(3-methyl-2,6-dioxo-4-(trifluoromethyl)-3,6-dihydropyrimidin-1(2H)-yl)-N-((1-methylcyclopropyl)sulfonyl)benzamide

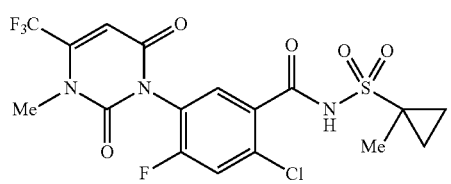

7

Prepared according to the procedure described for Intermediate G using Intermediate A (100.0 mg, 0.27 mmol), 1-methylcyclopropanesulfonamide (44.2 mg, 0.33 mmol), HATU (124.0 mg, 0.33 mmol) and N,N-diisopropylethylamine (0.14 mL, 0.82 mmol). The crude residue was purified by flash chromatography (SiO$_2$, 0-25% EtOAc (0.5% AcOH) in PE (0.5% AcOH)) to afford the title compound as a white solid (81.6 mg, 62%). $^1$H NMR $\delta_H$ (CDCl$_3$, 500 MHz) 7.65 (d, J=7.4 Hz, 1H), 7.60 (d, J=9.4 Hz, 1H), 6.46

(s, 1H), 3.53 (d, J=1.1 Hz, 3H), 1.63 (td, J=5.7, 0.9 Hz, 2H), 1.60 (s, 3H), 1.00-0.95 (m, 2H). LCMS (Method D): 7.43 min (483.9, [M+H]+).

Intermediate H: Ethyl (Z)-3-(3,3-dimethylureido)-4,4,4-trifluorobut-2-enoate

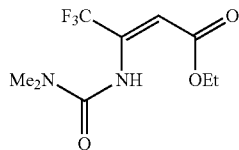

To a nitrogen purged suspension of sodium hydride (1.53 g, 38.2 mmol) in DMF (54.6 ml) at 0° C. was added ethyl 3-amino-4,4,4-trifluorocrotonate (5.0 g, 27.31 mmol, in 10 mL DMF) in a dropwise manner over a 30 min period and the reaction was allowed to proceed for 1 h. Dimethylcarbamyl chloride (7.54 ml, 82.0 mmol) was added in a dropwise manner over 30 min and the reaction was allowed to warm to r.t. before being heated to 60° C. for approx. 21 h under nitrogen. The reaction mixture was allowed to cool to room temperature before HCl (1 M, 50 mL) was slowly added to the reaction mixture and the solution was allowed to stir for 30 mins. Water (200 mL), EtOAc (50 mL) and sat. brine (25 mL) were then added and the two layers separated. The aqueous layer was re-extracted with 3×50 mL EtOAc and the combined organics were dried using $Na_2SO_4$, filtered and concentrated under reduced pressure to afford an orange oil. The residue was purified by flash chromatography ($SiO_2$, 7-60% EtOAc (0.5% AcOH) in PE (0.5% AcOH)) to afford the title compound as a pale yellow liquid (1.248 g, 18% yield). $^1$H NMR $\delta_H$ (CDCl$_3$, 500 MHz) 5.76-5.63 (m, 1H), 4.23 (q, J=7.1 Hz, 2H), 3.05 (s, 6H), 1.31 (t, J=7.1 Hz, 3H). LCMS (Method C): 2.38 min (255.1, [M+H]+).

Intermediate I: 2-(Dimethylamino)-4-(trifluoromethyl)-6H-1,3-oxazin-6-one

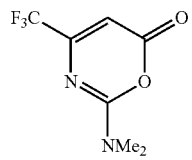

To a solution of ethyl (Z)-3-(3,3-dimethylureido)-4,4,4-trifluorobut-2-enoate (1.24 g, 4.91 mmol) in phosphorus(V) oxychloride (0.45 ml, 4.91 mmol) was added phosphorus pentachloride (1.02 g, 4.91 mmol) in five portions, giving time for the reaction mixture to fully homogenise between additions. The reaction was allowed to proceed at room temperature, monitoring by TLC every 15 minutes. After 45 min, the reaction was poured slowly in to a stirred flask of ice water (200 mL). Once the ice had melted, EtOAc (50 mL), sat. aq. NaHCO$_3$ (50 mL) and sat. brine (30 mL) were then added and the two layers separated. The aqueous layer was re-extracted with 3×20 mL EtOAc and the combined organics were dried using $Na_2SO_4$, filtered and concentrated under reduced pressure to afford the title compound as a yellow solid (874.4 mg, 86%). $^1$H NMR $\delta_H$(CDCl$_3$, 500 MHz) 5.86 (s, 1H), 3.22 (s, 3H), 3.17 (s, 3H). LCMS (Method C): 2.50 min (209.1, [M+H]+).

Intermediate J: 5-(2,6-Dioxo-4-(trifluoromethyl)-3,6-dihydropyrimidin-1(2H)-yl)-2,4-difluorobenzoic acid

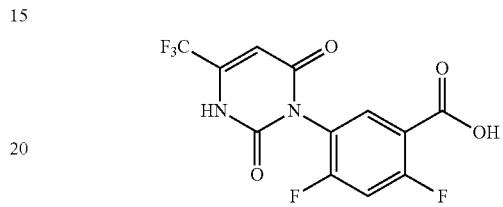

To a solution of Intermediate I (300.0 mg, 1.44 mmol) in acetic acid (14.4 mL) was added 5-amino-2,4-difluorobenzoic acid (262.0 mg, 1.51 mmol). The vial was capped and the reaction was heated to 90° C. for approx. 18 hours. To the reaction mixture was added water (50 mL), sat. brine (10 mL) and EtOAc (10 mL) and the layers separated. The aqueous layer was re-extracted with 3×10 mL EtOAc and the combined organics were dried with Na$_2$SO$_4$ and concentrated under reduced pressure to afford the title compound as a brown oil (206.1 mg, 43%). LCMS (Method C): 1.82 min (336.0, [M+H]+).

Intermediate K: Methyl 2,4-difluoro-5-(3-methyl-2,6-dioxo-4-(trifluoromethyl)-3,6-dihydropyrimidin-1(2H)-yl)benzoate

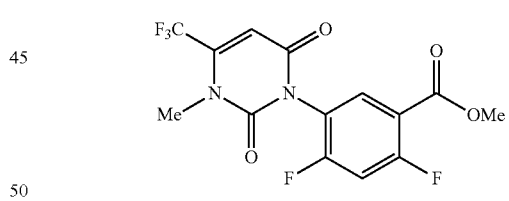

To a solution of Intermediate J (206.1 mg, 0.61 mmol) and potassium carbonate (424.0 mg, 3.07 mmol) in DMF (1.3 mL) was added iodomethane (0.38 mL, 6.13 mmol). The reaction was capped and heated to 60° C. for approx. 18 h. Ammonia (water solution, 5 mL) was added to quench excess iodomethane. Water (300 mL) and dichloromethane (50 mL) were added to the reaction mixture and the layers separated. The aqueous layer was re-extracted with 3×50 mL DCM and the combined organics were washed with water (3×50 mL), dried with Na$_2$SO$_4$ and concentrated under reduced pressure to afford the title compound as a brown solid (171.0 mg, 77%). $^1$H NMR $\delta_H$ (CDCl$_3$, 500 MHz) 7.98-7.92 (m, 1H), 7.07 (t, J=9.7 Hz, 1H), 6.38 (s, 1H), 3.92 (s, 3H), 3.57 (d, J=1.2 Hz, 3H). LCMS (Method C): 2.68 min (365.1, [M+H]+).

Intermediate L: 2,4-Difluoro-5-(3-methyl-2,6-dioxo-4-(trifluoromethyl)-3,6-dihydropyrimidin-1(2H)-yl)benzoic acid

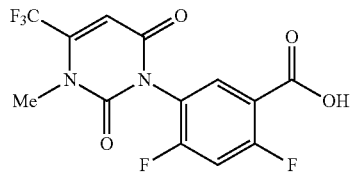 [SMILES: Cn1c(C(F)(F)F)cc(=O)n(-c2cc(C(=O)O)c(F)cc2F)c1=O]

To a 0° C. solution of Intermediate K (171.0 mg, 0.47 mmol) in DCM (2.3 mL) was added boron tribromide (1 M in DCM, 1.41 mL, 1.41 mmol) in a drop-wise manner. The reaction was allowed to proceed for 30 min before being removed from the ice bath and being allowed to proceed for approx. 18 h at r.t. The reaction mixture was added dropwise to a stirred flask containing ice water (10 mL). Once the ice had melted, DCM (10 mL) and sat. brine (5 mL) were then added to the resultant biphasic mixture. The aqueous layer was re-extracted with 3×20 mL DCM and the combined organics were then dried with $Na_2SO_4$ and concentrated under reduced pressure to afford the title compound a yellow solid (159.1 mg, 97%). LCMS (Method C): 2.20 min (351.1, $[M+H]^+$).

Example 8: N-(Cyclopropylsulfonyl)-2,4-difluoro-5-(3-methyl-2,6-dioxo-4-(trifluoromethyl)-3,6-dihydropyrimidin-1(2H)-yl)benzamide

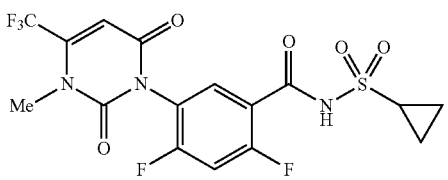

Prepared according to the procedure described for Intermediate G using Intermediate L (159.1 mg, 0.45 mmol), cyclopropanesulfonamide (60.5 mg, 0.50 mmol), HATU (207.0 mg, 0.55 mmol) and N,N-diisopropylethylamine (0.24 mL, 0.14 mmol). The crude residue was purified by passing it through a pad of silica, eluting with 0-30% EtOAc (0.5% AcOH) in PE (0.5% AcOH) to afford the title compound as a yellow solid (62.8 mg, 30%). $^1$H NMR $\delta_H$ (CDCl$_3$, 500 MHz) 8.71 (d, J=14.0 Hz, 1H), 8.11 (t, J=7.9 Hz, 1H), 7.15 (dd, J=11.3, 8.8 Hz, 1H), 6.38 (s, 1H), 3.57 (d, J=1.0 Hz, 3H), 3.09 (ddd, J=8.1, 4.8, 3.3 Hz, 1H), 1.49-1.46 (m, 2H), 1.19-1.16 (m, 2H). LCMS (Method D): 6.95 min (454.1, $[M+H]^+$).

Intermediate M: 2-Chloro-5-(2,6-dioxo-4-(trifluoromethyl)-3,6-dihydropyrimidin-1(2H)-yl)benzoic acid

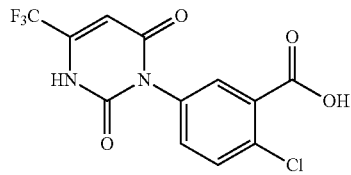 [SMILES: O=C(O)c1cc(-n2c(=O)cc(C(F)(F)F)[nH]c2=O)ccc1Cl]

Prepared according to the procedure described for Intermediate J using Intermediate I (500.0 mg, 2.40 mmol), acetic acid (2.4 mL) and 5-amino-2-chlorobenzoic acid (412.0 mg, 2.40 mmol) to afford the title compound as a yellow solid (206.1 mg, 43%). LCMS (Method C): 1.70 min (335.1, $[M+H]^+$).

Intermediate N: Methyl 2-chloro-5-(3-methyl-2,6-dioxo-4-(trifluoromethyl)-3,6-dihydropyrimidin-1(2H)-yl)benzoate

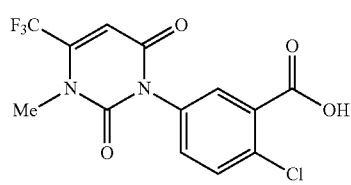 [SMILES: Cn1c(C(F)(F)F)cc(=O)n(-c2ccc(Cl)c(C(=O)O)c2)c1=O]

Prepared according to the procedure described for Intermediate K using Intermediate M (792.3 mg, 2.37 mmol), potassium carbonate (1.64 g, 11.84 mmol), DMF (2.4 mL) and iodomethane (1.47 mL, 23.68 mmol) to afford the title compound as a brown solid (822.2 mg, 96%). LCMS (Method C): 2.78 min (363.0, $[M+H]^+$).

Intermediate O: 2-Chloro-5-(3-methyl-2,6-dioxo-4-(trifluoromethyl)-3,6-dihydropyrimidin-1(2H)-yl)benzoic acid Prepared according to the procedure described for Intermediate L using Intermediate N (822.2 mg, 2.27 mmol), dichloromethane (11.3 mL) and boron tribromide (1 M in dichloromethane, 6.8 mL, 6.8 mmol) to afford the title compound a yellow solid (690.0 mg, 87%). LCMS (Method C): 1.95 min (349.1, $[M+H]^+$).

Example 9: 2-Chloro-5-(3-methyl-2,6-dioxo-4-(trifluoromethyl)-3,6-dihydropyrimidin-1(2H)-yl)-N-((1-methylcyclopropyl)sulfonyl)benzamide

Prepared according to the procedure described for Intermediate G using Intermediate O (200.0 mg, 0.57 mmol), 1-methylcyclopropanesulfonamide (78.0 mg, 0.57 mmol), HATU (262.0 mg, 0.69 mmol) and N,N-diisopropylethylamine (0.24 mL, 0.14 mmol). The crude residue was purified by passing it through a pad of silica, eluting with 0-30% EtOAc (0.5% AcOH) in PE (0.5% AcOH) to afford the title compound as a white solid (90.0 mg, 34%). $^1$H NMR $\delta_H$ (DMSO-d$_6$, 500 MHz) 12.43 (s, 1H), 7.69 (d, J=8.5 Hz, 1H), 7.53 (d, J=2.3 Hz, 1H), 7.49-7.42 (m, 1H), 6.56 (s, 1H), 3.39 (s, 3H), 1.52 (s, 3H), 1.45 (s, 2H), 1.23 (s, 1H), 0.99 (s, 2H). LCMS (Method D): 7.09 min (466.0, [M+H]$^+$).

Intermediate P: Tetrahydrothiophene-3-sulfonamide 1,1-dioxide

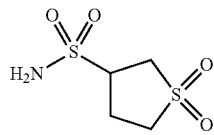

Prepared according to the procedure described in Example 1 using tetrahydro-3-thiophenesulfonyl chloride (1.0 g, 4.57 mmol), THF (28.6 ml) and ammonium hydroxide (6.4 ml, 45.7 mmol) to afford the title compound as a white solid (622.9 mg, 68%). $^1$H NMR $\delta_H$ (DMSO-d$_6$, 500 MHz) 7.24 (s, 2H), 4.02-3.93 (m, 1H), 3.49 (dd, J=14.0, 9.2 Hz, 1H), 3.34-3.18 (m, 3H), 2.48-2.41 (m, 1H), 2.37-2.27 (m, 1H).

Example 10: 2-Chloro-N-((1,1-dioxidotetrahydrothiophen-3-yl)sulfonyl)-4-fluoro-5-(3-methyl-2,6-dioxo-4-(trifluoromethyl)-3,6-dihydropyrimidin-1(2H)-yl)benzamide

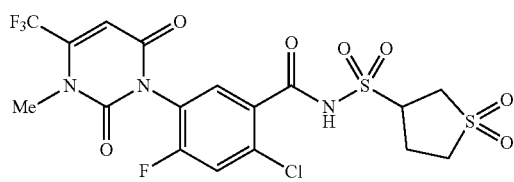

Prepared according to the procedure described in Example 1 using Intermediate A (200.0 mg, 0.545 mmol), Intermediate P (109.0 mg, 0.55 mmol), oxalyl chloride (0.14 mL, 1.64 mmol), isothiazolidine 1,1-dioxide (66.1 mg, 0.55 mmol), 4-(dimethylamino)pyridine (3.3 mg, 0.03 mmol) and triethylamine (0.27 mL, 1.91 mmol). The crude residue was purified by flash chromatography (SiO$_2$, 0-7.5% MeOH (0.5% AcOH) in dichloromethane (0.5% AcOH)) to afford the title compound as an orange solid (61.0 mg, 20%). $^1$H NMR $\delta_H$ (CDCl$_3$, 500 MHz) 7.75 (d, J=6.5 Hz, 1H), 7.42 (d, J=8.8 Hz, 1H), 6.37 (s, 1H), 4.86 (s, 1H), 4.72-4.57 (m, 1H), 3.57 (s, 3H), 3.44-3.33 (m, 2H), 3.25-3.13 (m, 2H), 2.74 (dd, J=14.2, 6.7 Hz, 2H). LCMS (Method D): 5.86 min (547.8, [M+H]$^+$).

Intermediate Q: Methyl 2,4-dichloro-5-nitrobenzoate

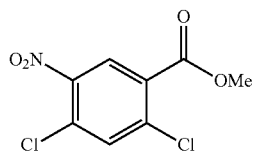 [SMILES: COC(=O)c1cc([N+](=O)[O-])c(Cl)cc1Cl]

To a flask of methyl 2,4-dichlorobenzoate (500.0 mg, 2.44 mmol) at 0° C. was added conc. sulfuric acid (2.73 mL, 51.2 mmol) and then conc. nitric acid (0.46 mL, 9.27 mmol) in a drop-wise manner. The reaction was allowed to warm to r.t. and to proceed for 18 h. The reaction mixture was carefully poured into a flask of stirred ice water (100 mL). Once the ice had melted, EtOAc (40 mL) and sat. brine (20 mL) were then added and the layers separated. The aqueous layer was re-extracted with 3×10 mL EtOAc washings and the combined organics were then dried with Na$_2$SO$_4$ and concentrated under reduced pressure to afford the title compound as a yellow solid (579.2 mg, 95%). $^1$H NMR $\delta_H$ (CDCl$_3$, 500 MHz) 7.75 (d, J=6.5 Hz, 1H), 7.42 (d, J=8.8 Hz, 1H), 6.37 (s, 1H), 4.86 (s, 1H), 4.72-4.57 (m, 1H), 3.57 (s, 3H), 3.44-3.33 (m, 2H), 3.25-3.13 (m, 2H), 2.74 (dd, J=14.2, 6.7 Hz, 2H).

Intermediate R: Methyl 5-amino-2,4-dichlorobenzoate

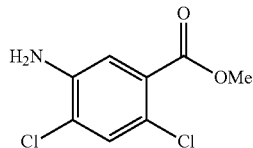

A mixture of Intermediate Q (580.0 mg, 2.32 mmol), iron powder (259.0 mg, 4.64 mmol), ammonium chloride (869.0 mg, 16.24 mmol), methanol (1.55 mL) and water (3.09 mL) was purged with nitrogen and heated to 90° C. for 18 h. The crude solution was filtered through a pad of Celite®, eluting with 50% EtOAc in petroleum ether to afford a filtrate which was then dried with Na$_2$SO$_4$, filtered and concentrated under reduced pressure to afford the title compound as an orange solid (339.0 mg, 66%). $^1$H NMR $\delta_H$ (CDCl$_3$, 500 MHz) 7.35 (s, 1H), 7.26 (s, 1H), 3.90 (s, 3H). LCMS (Method C): 2.70 min (220.0, [M+H]$^+$).

Intermediate S: 5-Amino-2,4-dichlorobenzoic acid

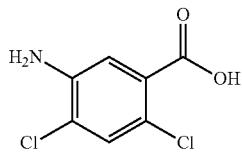 [SMILES: Nc1cc(C(=O)O)c(Cl)cc1Cl]

A solution of Intermediate R (339.0 mg, 1.54 mmol) in methanol (4.67 mL) was added 1 M aq. sodium hydroxide (4.6 mL, 4.6 mmol). The reaction was then allowed to proceed at r.t. for approx. 18 h. Water (20 mL) and 1 M HCl (4 mL) were added to the reaction and the solution was brought to approx. pH 6. EtOAc (50 mL) was then added and the layers separated. The aqueous layer was re-extracted with EtOAc (3×10 mL) and the combined organics were dried using $Na_2SO_4$ and concentrated under reduced pressure to afford the title compound as a yellow solid (308.4 mg, 97%). $^1$H NMR $\delta_H$ (CDCl$_3$, 500 MHz) 13.25 (s, 1H), 7.38 (s, 1H), 7.23 (s, 1H), 5.75 (s, 2H).

Intermediate T: 2,4-Dichloro-5-(2,6-dioxo-4-(trifluoromethyl)-3,6-dihydropyrimidin-1(2H)-yl)benzoic acid

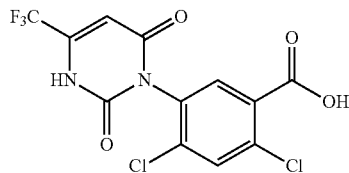 [SMILES: O=C(O)c1cc(-n2c(=O)cc(C(F)(F)F)[nH]c2=O)c(Cl)cc1Cl]

Prepared according to the procedure described for Intermediate J using Intermediate R (331.0 mg, 1.60 mmol), Intermediate I(318.0 mg, 1.53 mmol) and acetic acid (1.5 mL) to afford the title compound as an orange solid (455.7 mg, 81%). $^1$H NMR $\delta_H$ (DMSO-d$_6$, 500 MHz) 13.82 (s, 1H), 12.84 (s, 1H), 8.06 (s, 1H), 8.00 (s, 1H), 6.47 (s, 1H).

Intermediate U: Methyl 2,4-dichloro-5-(3-methyl-2,6-dioxo-4-(trifluoromethyl)-3,6-dihydropyrimidin-1(2H)-yl)benzoate

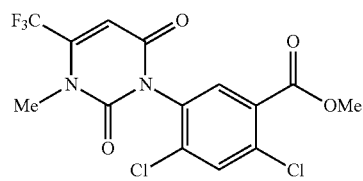 [SMILES: COC(=O)c1cc(-n2c(=O)cc(C(F)(F)F)n(C)c2=O)c(Cl)cc1Cl]

Prepared according to the procedure described for Intermediate N using Intermediate T (495.0 mg, 1.34 mmol), potassium carbonate (927.0 mg, 6.71 mmol) in DMF (1.34 mL) and iodomethane (0.84 mL, 13.41 mmol) to afford the title compound as a brown solid (429.7 mg, 81%). $^1$H NMR $\delta_H$ (CDCl$_3$, 500 MHz) 7.86 (s, 1H), 7.69 (s, 1H), 6.38 (s, 1H), 3.88 (m, 3H), 3.57 (d, J=1.0 Hz, 3H).

Intermediate V: 2,4-Dichloro-5-(3-methyl-2,6-dioxo-4-(trifluoromethyl)-3,6-dihydropyrimidin-1(2H)-yl)benzoic acid

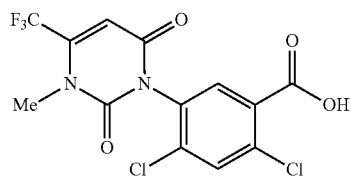 [SMILES: Cn1c(C(F)(F)F)cc(=O)n(-c2cc(C(=O)O)c(Cl)cc2Cl)c1=O]

Prepared according to the procedure described for Intermediate L using Intermediate U (429.7 mg, 1.08 mmol), dichloromethane (5.4 mL) and boron tribromide (1 M in dichloromethane, 3.25 mL, 3.25 mmol) to afford the title compound a white solid (400.5 mg, 97%). LCMS (Method C): 2.63 min (383.0, [M+H]$^+$).

Example 11: 2,4-Dichloro-5-(3-methyl-2,6-dioxo-4-(trifluoromethyl)-3,6-dihydropyrimidin-1(2H)-yl)-N-((1-methylcyclopropyl)sulfonyl)benzamide

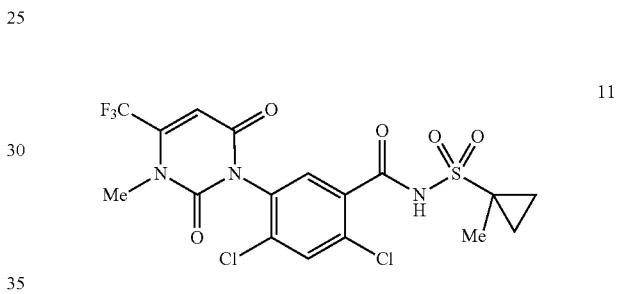

Prepared according to the procedure described for Intermediate G using Intermediate V (415.0 mg, 1.08 mmol), 1-methylcyclopropanesulfonamide (146.0 mg, 1.08 mmol), HATU (494.0 mg, 1.30 mmol) and N,N-diisopropylethylamine (0.57 mL, 0.33 mmol). The crude residue was purified by flash chromatography (SiO$_2$, 0-30% EtOAc (0.5% AcOH) in PE (0.5% AcOH)) to afford the title compound as an off-white solid (154.4 mg, 29%). $^1$H NMR $\delta_H$ (DMSO-d$_6$, 500 MHz) 12.54 (s, 1H), 8.05 (s, 1H), 7.78 (s, 1H), 6.66 (s, 1H), 3.43 (s, 3H), 1.52 (s, 3H), 1.46 (s, 2H), 1.23 (s, 1H), 1.01 (s, 2H). LCMS (Method D): 7.77 min (499.9, [M+H]$^+$).

Example 12: 2-Chloro-N-(cyclopropylsulfonyl)-4-fluoro-5-(3-methyl-2,6-dioxo-4-(trifluoromethyl)-3,6-dihydropyrimidin-1(2H)-yl)benzamide

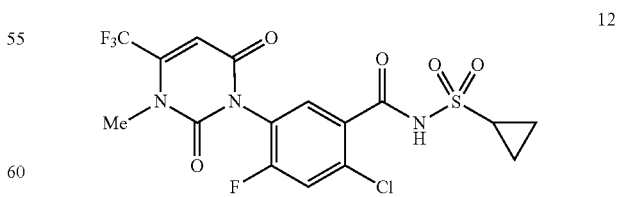

Prepared according to the procedure described for Example 1 using Intermediate A (200.0 mg, 0.55 mmol), cyclopropylsulfonamide (86.0 mg, 0.71 mmol), oxalyl chloride (0.14 mL, 1.64 mmol), 4-(dimethylamino)pyridine (5.0 mg, 0.04 mmol) and triethylamine (0.29 mL, 2.05 mmol).

The residue was purified by flash chromatography (SiO₂, 10-50% EtOAc (0.1% AcOH) in PE (0.1% AcOH)) to afford the title compound as a white solid (115.0 mg, 45%). ¹H NMR δ$_H$ (CDCl₃, 400 MHz) 8.77 (s, 1H), 7.81 (d, J=7.5 Hz, 1H), 7.42 (d, J=9.0 Hz, 1H), 6.39 (s, 1H), 3.58 (s, 1H), 3.11 (tt, J=8.0, 5.0 Hz, 1H), 1.52-1.48 (m, 2H), 1.23-1.18 (m, 2H). LCMS (Method C): 1.69 min (469.9, [M+H]⁺).

Example 13: 2-Chloro-N-(cyclopentylsulfonyl)-4-fluoro-5-(3-methyl-2,6-dioxo-4-(trifluoromethyl)-3,6-dihydropyrimidin-1(2H)-yl)benzamide

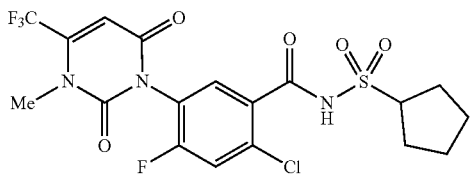

Prepared according to the procedure described for Example 1 using Intermediate A (200.0 mg, 0.55 mmol), cyclopentylsulfonamide (82.0 mg, 0.55 mmol), oxalyl chloride (0.14 mL, 1.64 mmol), 4-(dimethylamino)pyridine (5.0 mg, 0.04 mmol) and triethylamine (0.29 mL, 2.05 mmol). The residue was purified by flash chromatography (SiO₂, 20-50% EtOAc in PE) to afford the title compound as an off-white solid (90.0 mg, 33%). ¹H NMR δ$_H$ (CDCl₃, 400 MHz) 8.63 (s, 1H), 7.80 (d, J=7.5 Hz, 1H), 7.42 (d, J=9.0 Hz, 1H), 6.39 (s, 1H), 4.31-4.23 (m, 1H), 3.59 (s, 1H), 2.24-2.09 (m, 5H), 1.93-1.84 (m, 2H), 1.78-1.70 (m, 2H). LCMS (Method C): 1.82 min (496.0, [M–H]⁻).

Example 14: 2-Chloro-N-(cyclohexylsulfonyl)-4-fluoro-5-(3-methyl-2,6-dioxo-4-(trifluoromethyl)-3,6-dihydropyrimidin-1(2H)-yl)benzamide

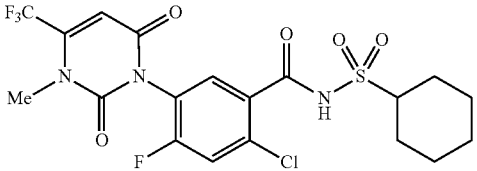

Prepared according to the procedure described for Example 1 using Intermediate A (150.0 mg, 0.41 mmol), cyclohexylsulfonamide (87.0 mg, 0.53 mmol), oxalyl chloride (0.10 mL, 1.23 mmol), 4-(dimethylamino)pyridine (4.0 mg, 0.03 mmol) and triethylamine (0.21 mL, 1.53 mmol). The residue was purified by flash chromatography (SiO₂, 10-40% EtOAc (0.1% AcOH) in PE (0.1% AcOH)) to afford the title compound as a white solid (60.0 mg, 29%). ¹H NMR δ$_H$ (CDCl₃, 300 MHz) 8.72 (s, 1H), 7.68 (d, J=6.0 Hz, 1H), 7.33 (d, J=6.0 Hz, 1H), 6.30 (s, 1H), 3.72-3.56 (m, 1H), 3.49 (s, 3H), 2.26-2.02 (m, 2H), 1.89-1.85 (m, 2H), 1.65-1.57 (m, 4H), 1.48-1.17 (m, 2H). LCMS (Method C): 2.00 min (512.0, [M+H]⁺).

Intermediate W: 3-(2,6-Dioxo-4-(trifluoromethyl)-3,6-dihydropyrimidin-1(2H)-yl)-4-fluorobenzoic acid

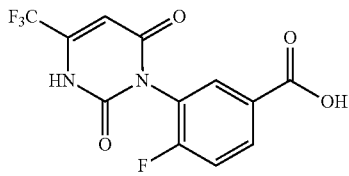 [SMILES: O=C(O)c1ccc(F)c(-n2c(=O)cc(C(F)(F)F)[nH]c2=O)c1]

Prepared according to the procedure described for Intermediate J using Intermediate 1 (300.0 mg, 1.44 mmol) and acetic acid (14.4 mL) was added 3-amino-4-fluorobenzoic acid (235 mg, 1.51 mmol) to afford the title compound as a yellow oil (137.5 mg, 29% yield) which was used without further purification.

Intermediate X: Methyl 4-fluoro-3-(3-methyl-2,6-dioxo-4-(trifluoromethyl)-3,6-dihydropyrimidin-1(2H)-yl)benzoate

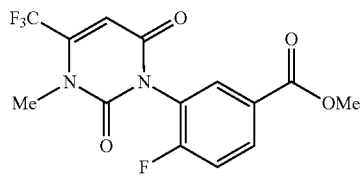 [SMILES: COC(=O)c1ccc(F)c(-n2c(=O)cc(C(F)(F)F)n(C)c2=O)c1]

Prepared according to the procedure described for Intermediate K using Intermediate W (137 mg, 0.432 mmol) and potassium carbonate (299 mg, 2.16 mmol) and DMF (1.4 mL) to afford the title compound as a brown solid (125.4 mg, 84% yield). ¹H NMR δ$_H$ (CDCl₃, 500 MHz) 8.17 (ddd, J=8.7, 4.9, 2.2 Hz, 1H), 8.00 (dd, J=7.0, 2.1 Hz, 1H), 7.31 (t, J=8.9 Hz, 1H), 6.38 (s, 1H), 3.91 (s, 3H), 3.57 (d, J=1.2 Hz, 3H). LCMS (Method C): 2.63 min (347.1, [M+H]⁺).

Intermediate Y: 4-Fluoro-3-(3-methyl-2,6-dioxo-4-(trifluoromethyl)-3,6-dihydropyrimidin-1(2H)-yl)benzoic acid

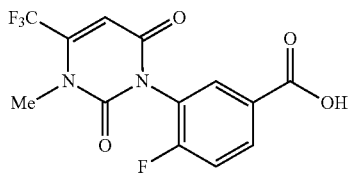 [SMILES: Cn1c(C(F)(F)F)cc(=O)n(-c2cc(C(=O)O)ccc2F)c1=O]

Prepared according to the procedure described for Intermediate L using Intermediate X (125 mg, 0.362 mmol), dichloromethane (1.8 mL) and boron tribromide (1 M in dichloromethane, 1.09 mL, 1.09 mmol) to afford the title compound a brown solid (101.2 mg, 85% yield). ¹H NMR δ$_H$(CDCl₃, 500 MHz) 8.22 (ddd, J=8.7, 4.8, 2.2 Hz, 1H), 8.06 (dd, J=6.9, 2.1 Hz, 1H), 7.34 (t, J=8.9 Hz, 1H), 6.40 (s, 1H), 3.58 (d, J=0.9 Hz, 3H). LCMS (Method C): 2.22 min (333.1, [M+H]⁺).

Example 15: N-(Cyclopropylsulfonyl)-4-fluoro-3-(3-methyl-2,6-dioxo-4-(trifluoromethyl)-3,6-dihydropyrimidin-1(2H)-yl)benzamide

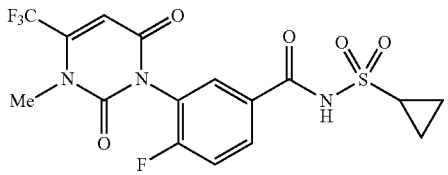 [SMILES: Cn1c(C(F)(F)F)cc(=O)n(-c2cc(C(=O)NS(=O)(=O)C3CC3)ccc2F)c1=O]

Prepared according to the procedure described for Intermediate G using Intermediate Y (385.3 mg, 1.160 mmol), cyclopropane sulfonamide (155 mg, 1.28 mmol), HATU (529 mg, 1.39 mmol) and N,N-diisopropylethylamine (0.606 mL, 3.48 mmol). The crude residue was purified by flash chromatography (SiO$_2$, 0-30% EtOAc (0.5% AcOH) in PE (0.5% AcOH)) to afford the title compound as an off-white solid (244.1 mg, 48% yield). $^1$H NMR $\delta_H$ (CDCl$_3$, 500 MHz) 8.89 (s, 1H), 7.96 (ddd, J=8.7, 4.6, 2.3 Hz, 1H), 7.81 (dd, J=6.6, 2.3 Hz, 1H), 7.34 (t, J=8.8 Hz, 1H), 6.39 (s, 1H), 3.58 (s, 3H), 3.13-3.05 (m, 1H), 1.47-1.40 (m, 2H), 1.16 (qd, J=6.3, 1.6 Hz, 2H). LCMS (Method D): 6.67 min (435.9, [M+H]$^+$).

Example 16: 2-Chloro-4-fluoro-N-((1-fluorocyclopropyl)sulfonyl)-5-(3-methyl-2,6-dioxo-4-(trifluoromethyl)-3,6-dihydropyrimidin-1(2H)-yl)benzamide

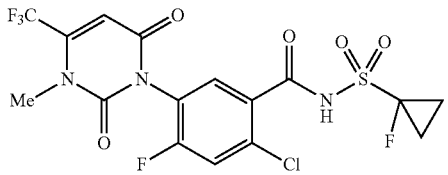 [SMILES: Cn1c(C(F)(F)F)cc(=O)n(-c2cc(C(=O)NS(=O)(=O)C3(F)CC3)c(Cl)cc2F)c1=O]

Prepared according to the procedure described for Intermediate G using Intermediate A (200 mg, 0.6 mmol), 1-fluorocyclopropane-1-sulfonamide (95 mg, 0.68 mmol), HATU (259 mg, 0.682 mmol) and N,N-diisopropylethylamine (0.285 mL, 1.64 mmol). The crude residue was purified by flash chromatography (SiO$_2$, 0-25% EtOAc (0.5% AcOH) in PE (0.5% AcOH)) to afford the title compound as an off-white solid (180.2 mg, 68% yield). $^1$H NMR $\delta_H$ (CDCl$_3$, 500 MHz) 9.59 (s, 1H), 7.71 (d, J=7.4 Hz, 1H), 7.41 (d, J=8.9 Hz, 1H), 6.40 (s, 1H), 3.56 (s, 3H), 1.93 (m, 2H), 1.58 (dt, J=16.7, 8.3 Hz, 2H). LCMS (Method F): 1.99 min (488.0, [M+H]$^+$).

Example 17: 2-Chloro-N-((1-ethylcyclopropyl)sulfonyl)-4-fluoro-5-(3-methyl-2,6-dioxo-4-(trifluoromethyl)-3,6-dihydropyrimidin-1(2H)-yl)benzamide

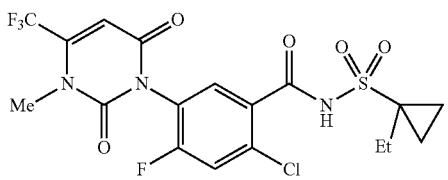 [SMILES: CCC1(S(=O)(=O)NC(=O)c2cc(-n3c(=O)cc(C(F)(F)F)n(C)c3=O)c(F)cc2Cl)CC1]

Prepared according to the procedure described for Intermediate G using Intermediate A (200 mg, 0.6 mmol), 1-ethylcyclopropane-1-sulfonamide (102 mg, 0.682 mmol), HATU (259 mg, 0.682 mmol) and N,N-diisopropylethylamine (0.285 mL, 1.64 mmol). The crude residue was purified by flash chromatography (SiO$_2$, 0-25% EtOAc (0.5% AcOH) in PE (0.5% AcOH)) to afford the title compound as a white solid (23.5 mg, 9% yield). $^1$H NMR $\delta_H$ (CDCl$_3$, 500 MHz) 8.67 (s, 1H), 7.80 (d, J=7.4 Hz, 1H), 7.43 (d, J=8.9 Hz, 1H), 6.40 (s, 1H), 3.59 (s, 3H), 2.04 (q, J=7.5 Hz, 2H), 1.79 (m, 2H), 1.07 (m, 5H). LCMS (Method F): 1.88 min (498.0, [M+H]$^+$).

Example 18—Testing the Herbicidal Activity of Compounds of the Invention

Compounds were screened at four concentrations (100, 50, 25 and 12.5 g/ha) against four weed species (*Stellaria media*—Chickweed; *Abutilon theophrasti*—velvetleaf; *Amaranthus retroflexus*—common amaranthus; *Echinochloa crus-galli*—Barnyard grass) and maize as a crop species.

Seed were sown in 12.5 cm diameter pots (20 per pot for the weed species and 5 for maize).

Seedlings were sprayed with 2 ml of compound two weeks after sowing, with 2 ml water used as the control.

Each treatment was replicated three times. Plants were maintained at 20° C. and assessed 10 days after treatment.

The assessment was based on the % plant in each pot showing growth. The data is presented in Table 1 in which d represents no detected effect at this concentration; c represents a percentage increase in necrosis relative to the control of 0.1-50; b represents a percentage increase in necrosis of 50-80; and a represents a percentage increase in necrosis of 80-100.

All of the compounds showed some herbicidal activity against the weed species but comparatively little activity against the crop species (maize). Certain compounds (2, 5, 7, 13, 14, 16, 17) showed good activity across several of the weed species.

TABLE 1

| Plant species | Dose applied (g/ha) | 1 | 2 | 4 | 5 | 6 | 7 | 8 | 10 | 12 | 13 | 14 | 15 | 16 | 17 |
|---|---|---|---|---|---|---|---|---|---|---|---|---|---|---|---|
| Chickweed | 100 | c | a | b | b | b | a | b | c | c | c | a | c | a | a |
| | 50 | c | b | c | b | c | b | c | c | c | c | b | d | c | b |
| | 25 | c | b | c | c | c | b | c | c | c | c | c | d | c | b |
| | 12.5 | c | b | c | c | c | c | c | c | c | c | c | d | c | c |
| Abutilon | 100 | b | a | b | a | b | a | b | c | b | a | a | b | a | a |
| | 50 | b | b | c | a | b | a | b | c | c | b | a | b | b | b |
| | 25 | b | b | c | b | c | a | c | c | c | b | b | c | c | c |
| | 12.5 | c | b | c | c | c | c | c | c | c | c | b | d | c | c |
| Amaranthus | 100 | a | a | a | a | a | a | a | b | a | a | a | b | a | a |
| | 50 | b | a | a | a | a | a | a | b | a | a | a | b | a | a |
| | 25 | b | a | b | a | b | a | c | b | b | b | a | d | c | b |
| | 12.5 | c | a | b | a | b | a | c | b | b | b | a | d | c | c |
| Echinochloa | 100 | c | a | c | b | c | a | b | c | c | c | c | c | b | b |
| | 50 | c | b | c | c | c | b | b | c | c | c | c | c | b | b |
| | 25 | c | b | c | c | c | c | c | c | c | c | c | d | c | b |
| | 12.5 | c | c | c | c | c | c | c | c | c | c | c | d | c | c |
| Maize | 100 | c | b | c | c | c | b | c | c | c | c | c | c | c | c |
| | 50 | c | b | c | c | c | c | c | c | c | c | c | c | c | c |
| | 25 | c | c | c | c | c | c | c | c | c | c | c | d | c | c |
| | 12.5 | c | c | c | c | c | c | c | c | c | c | c | d | c | c |

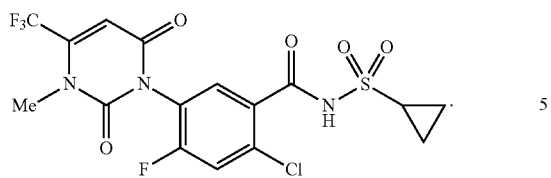
27. A herbicidal composition of claim 23, wherein the compound of formula (I) is:
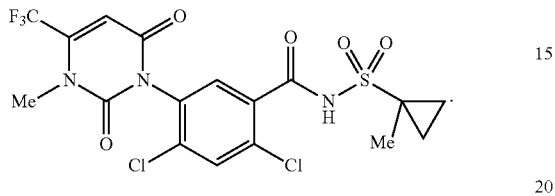

The invention claimed is:
1. A compound of formula I:

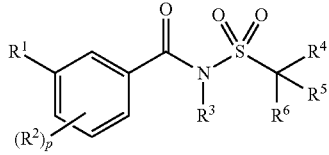

wherein
R¹ has the structure

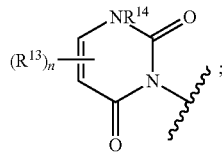

R$^{13}$ is independently at each occurrence selected from C$_1$-C$_6$-alkyl, C$_1$-C$_6$-haloalkyl, halogen, nitro, OR$^{10}$, SR$^{10}$, cyano, C$_2$-C$_6$-alkenyl, C$_2$-C$_6$-alkynyl, C$_3$-C$_6$-cycloalkyl and NR$^{10}$R$^{11}$; R$^{14}$ is independently selected from H and C$_1$-C$_6$-alkyl; and n is an integer independently selected from 0, 1 and 2;
R$^2$ is independently at each occurrence selected from C$_1$-C$_6$-alkyl, C$_1$-C$_6$-haloalkyl, halogen, nitro, OR$^{10}$, SR$^{10}$, OS(O)$_2$R$^{10}$, S(O)$_2$R$^{10}$, S(O)$_2$NR$^{10}$R$^{10}$, S(O)(NR$^{10}$)R$^{10}$, S(O)R$^{10}$, cyano, C$_2$-C$_6$-alkenyl, C$_2$-C$_6$-alkynyl, C$_3$-C$_6$-cycloalkyl, C$_3$-C$_6$-heterocycloalkyl and NR$^{10}$R$^{11}$;
R$^3$ is independently selected from: H, C$_1$-C$_6$-alkyl and C$_3$-C$_6$-cycloalkyl;
R$^4$ is independently selected from H, fluoro, chloro, C$_1$-C$_6$-haloalkyl and C$_1$-C$_6$-alkyl;
R$^5$ and R$^6$ together with the carbon atom to which they are attached form a cyclic group selected from C$_3$-C$_8$-cycloalkyl and 4- to 8-membered heterocycloalkyl; wherein the cyclic group is optionally substituted with from 1 to 4 R$^{12}$ groups;
R$^7$ and R$^{12}$ are independently at each occurrence selected from: =O, =S, C$_1$-C$_6$-alkyl, C$_1$-C$_6$-haloalkyl, halogen, nitro, OR$^{10}$, SR$^{10}$, S(O)$_2$R$^{10}$, S(O)$_2$NR$^{10}$R$^{10}$, S(O)(NR$^{10}$)R$^{10}$, S(O)R$^{10}$, C(O)R$^{10}$, C(O)NR$^{10}$R$^{10}$, C(O)OR$^{10}$, cyano, C$_2$-C$_6$-alkenyl, C$_2$-C$_6$-alkynyl, C$_3$-C$_6$-cycloalkyl, 3-to 6-membered heterocycloalkyl and NR$^{10}$R$^{11}$;
R$^{10}$ is independently at each occurrence selected from: H and C$_1$-C$_6$-alkyl;
R$^{11}$ is independently at each occurrence selected from; H, C$_1$-C$_6$-alkyl, C(O)—C$_1$-C$_6$-alkyl and S(O)$_2$-C$_1$-C$_6$-alkyl;
p is an integer independently selected from 0, 1, 2 and 3;
wherein any R$^2$, R$^3$, R$^4$, R$^7$, R$^{10}$, R$^{11}$, R$^{12}$ group that is alkyl, cycloalkyl, or heterocycloalkyl is optionally substituted, where chemically possible, by 1 to 4 substituents which are each independently selected at each occurrence from the group consisting of: =O; =NR$^a$, =NOR$^a$, C$_1$-C$_6$-alkyl, halo, nitro, cyano, C$_1$-C$_6$-haloalkyl, C$_2$-C$_6$-alkenyl, C$_2$-C$_6$-alkynyl, NR$^a$R$^b$, S(O)$_2$R$^a$, S(O)R$^a$, S(O)(NR$^a$)R$^a$, S(O)$_2$NR$^a$R$^a$, CO$_2$R$^a$, C(O)R$^a$, CONR$^a$R$^a$ and OR$^a$;

wherein R$^a$ is independently selected from H and C$_1$-C$_6$-alkyl; and R$^b$ is independently H, C$_1$-C$_6$-alkyl, C(O)—C$_1$-C$_6$-alkyl, or S(O)$_2$-C$_1$-C$_6$-alkyl;
or an agronomically acceptable salt or N-oxide thereof.
2. A compound of claim 1, wherein R$^1$ has the structure:

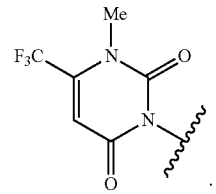

3. A compound of claim 1 wherein R$^3$ is H.
4. A compound of claim 1 wherein R$^4$ is H.
5. A compound of claim 1, wherein R$^4$ is independently selected from fluoro, C$_1$-C$_6$-haloalkyl and C$_1$-C$_6$-alkyl.
6. A compound of claim 1, wherein R$^5$ and R$^6$ together with the carbon atom to which they are attached form a C$_3$-C$_6$-cycloalkyl group; wherein the cycloalkyl group is optionally substituted with from 1 to 4 R$^{12}$ groups.
7. A compound of claim 6, wherein R$^5$ and R$^6$ together with the carbon atom to which they are attached form a cyclopropyl group; wherein the cyclopropyl group is optionally substituted with from 1 to 4 R$^{12}$ groups.
8. A compound of claim 6, wherein R$^5$ and R$^6$ together with the carbon atom to which they are attached form a cyclobutyl group; wherein the cyclobutyl group is optionally substituted with from 1 to 4 R$^{12}$ groups.
9. A compound of claim 6, wherein R$^5$ and R$^6$ together with the carbon atom to which they are attached form a cyclopentyl group; wherein the cyclopentyl group is optionally substituted with from 1 to 4 R$^{12}$ groups.
10. A compound of claim 6, wherein R$^5$ and R$^6$ may together with the carbon atom to which they are attached form a cyclohexyl group; wherein the cyclohexyl group is optionally substituted with from 1 to 4 R$^{12}$ groups.
11. A compound of claim 1, wherein the compound of formula (I) is selected from:

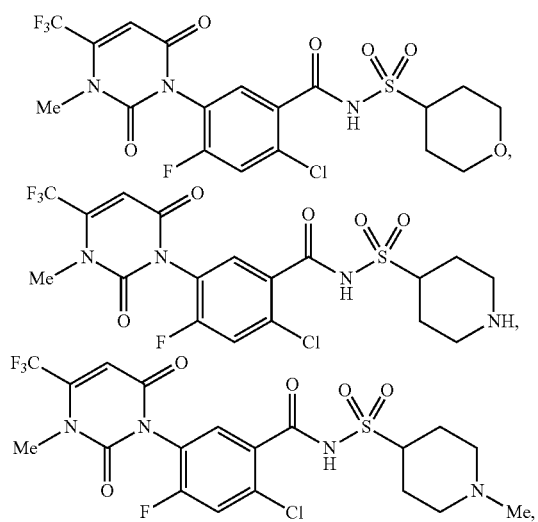

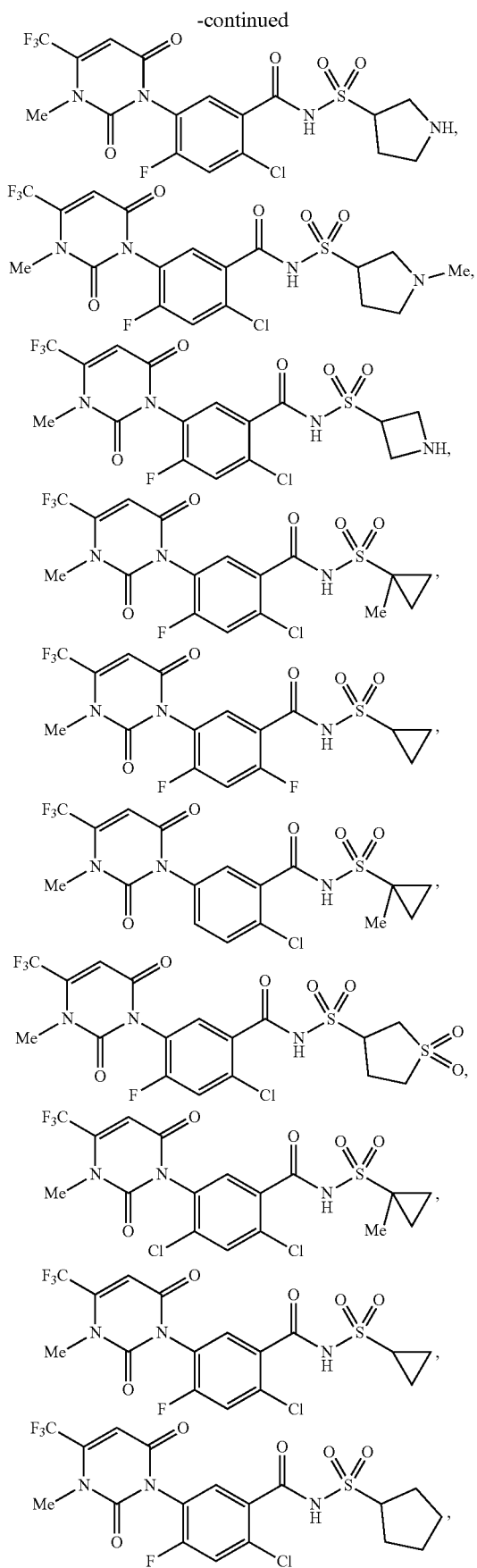
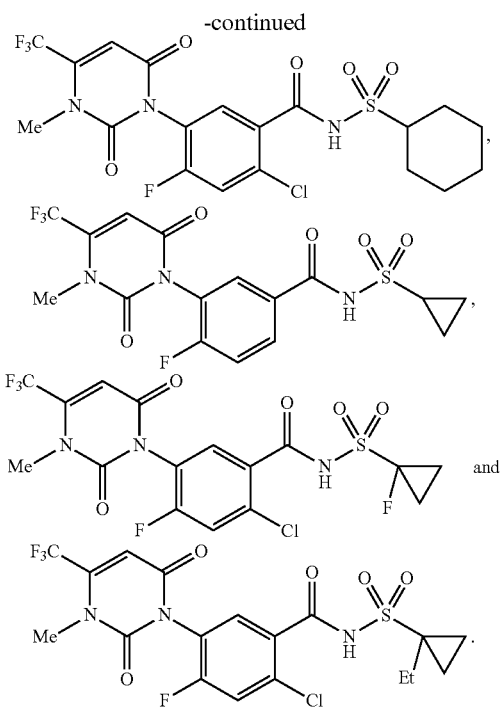
12. A compound of claim 11, wherein the compound of formula (I) is:
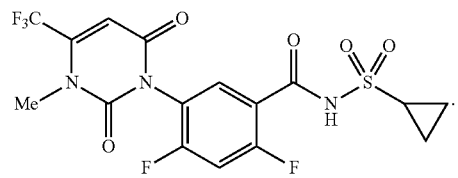
13. A compound of claim 11, wherein the compound of formula (I) is:
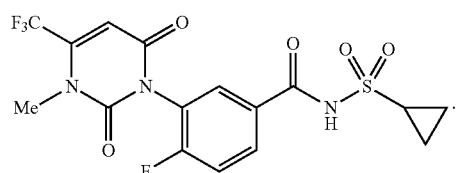
14. A compound of claim 11, wherein the compound of formula (I) is:
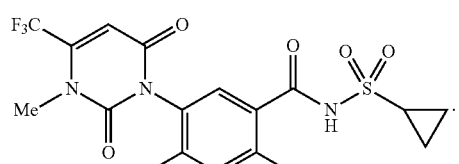
15. A compound of claim 11, wherein the compound of formula (I) is:

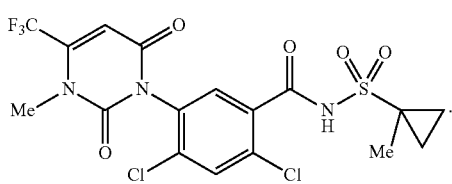 [SMILES: Cn1c(C(F)(F)F)cc(=O)n(-c2cc(C(=O)NS(=O)(=O)C3(C)CC3)c(Cl)cc2Cl)c1=O]

16. A herbicidal composition comprising an effective amount of an active compound of formula I:

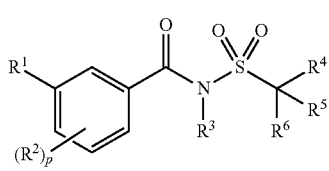

wherein
$R^1$ is selected from 5- to 9-membered bicyclic or monocyclic heterocycloalkyl group and 5-, 6-, 9- or 10-membered heteroaryl group; wherein said heterocycloalkyl or heteroaryl group comprises at least one nitrogen atom in the ring and is optionally substituted with from 1 to 6 $R^7$ groups;

or wherein $R^1$ is —N=$CR^8R^9$ wherein $R^8$ and $R^9$ together with the carbon atom to which they are attached form a 5- to 9-membered bicyclic or monocyclic heterocycloalkyl group; wherein said heterocycloalkyl group comprises at least one nitrogen atom in the ring and is optionally substituted with from 1 to 6 $R^7$ groups;

$R^2$ is independently at each occurrence selected from $C_1$-$C_6$-alkyl, $C_1$-$C_6$-haloalkyl, halogen, nitro, $OR^{10}$, $SR^{10}$, $OS(O)_2R^{10}$, $S(O)_2R^{10}$, $S(O)_2NR^{10}R^{10}$, $S(O)(NR^{10})R^{10}$, $S(O)R^{10}$, cyano, $C_2$-$C_6$-alkenyl, $C_2$-$C_6$-alkynyl, $C_3$-$C_6$-cycloalkyl, $C_3$-$C_6$-heterocycloalkyl and $NR^{10}R^{11}$;

$R^3$ is independently selected from: H, $C_1$-$C_6$-alkyl and $C_3$-$C_6$-cycloalkyl;

$R^4$ is independently selected from H, fluoro, chloro, $C_1$-$C_6$-haloalkyl and $C_1$-$C_6$-alkyl;

$R^5$ and $R^6$ together with the carbon atom to which they are attached form a cyclic group selected from $C_3$-$C_8$-cycloalkyl and 4- to 8-membered heterocycloalkyl; wherein the cyclic group is optionally substituted with from 1 to 4 $R^{12}$ groups;

$R^7$ and $R^{12}$ are independently at each occurrence selected from: =O, =S, $C_1$-$C_6$-alkyl, $C_1$-$C_6$-haloalkyl, halogen, nitro, $OR^{10}$, $SR^{10}$, $S(O)_2R^{10}$, $S(O)_2NR^{10}R^{10}$, $S(O)(NR^{10})R^{10}$, $S(O)R^{10}$, $C(O)R^{10}$, $C(O)NR^{10}R^{10}$, $C(O)OR^{10}$, cyano, $C_2$-$C_6$-alkenyl, $C_2$-$C_6$-alkynyl, $C_3$-$C_6$-cycloalkyl, 3-to 6-membered heterocycloalkyl and $NR^{10}R^{11}$;

$R^{10}$ is independently at each occurrence selected from: H and $C_1$-$C_6$-alkyl;

$R^{11}$ is independently at each occurrence selected from; H, $C_1$-$C_6$-alkyl, C(O)—$C_1$-$C_6$-alkyl and $S(O)_2$-$C_1$-$C_6$-alkyl;

p is an integer independently selected from 0, 1, 2 and 3;
wherein any $R^2$, $R^3$, $R^4$, $R^7$, $R^{10}$, $R^{11}$, $R^{12}$ group that is alkyl, cycloalkyl, or heterocycloalkyl is optionally substituted, where chemically possible, by 1 to 4 substituents which are each independently selected at each occurrence from the group consisting of: =O; =$NR^a$, =$NOR^a$, $C_1$-$C_6$-alkyl, halo, nitro, cyano, $C_1$-$C_6$-haloalkyl, $C_2$-$C_6$-alkenyl, $C_2$-$C_6$-alkynyl, $NR^aR^b$, $S(O)_2R^a$, $S(O)R^a$, $S(O)(NR^a)R^a$, $S(O)_2NR^aR^a$, $CO_2R^a$, $C(O)R^a$, $CONR^aR^a$ and $OR^a$;

wherein $R^a$ is independently selected from H and $C_1$-$C_6$-alkyl; and $R^b$ is independently H, $C_1$-$C_6$-alkyl, C(O)—$C_1$-$C_6$-alkyl, or $S(O)_2$-$C_1$-$C_6$-alkyl;

or an agronomically acceptable salt or N-oxide thereof.

17. A herbicidal composition of claim 16, wherein $R^1$ has the structure:

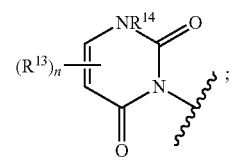

wherein $R^{13}$ is independently at each occurrence selected from $C_1$-$C_6$-alkyl, $C_1$-$C_6$-haloalkyl, halogen, nitro, $OR^{10}$, $SR^{10}$, cyano, $C_2$-$C_6$-alkenyl, $C_2$-$C_6$-alkynyl, $C_3$-$C_6$-cycloalkyl and $NR^{10}R^{11}$;

$R^{14}$ is independently selected from H and $C_1$-$C_6$-alkyl; and n is an integer independently selected from 0, 1 and 2.

18. A herbicidal composition of claim 16, wherein $R^1$ has the structure:

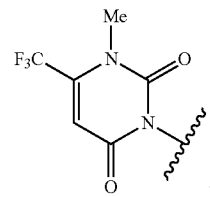

19. A herbicidal composition of claim 16 wherein $R^3$ is H.
20. A herbicidal composition of claim 16 wherein $R^4$ is H.
21. A herbicidal composition of claim 16, wherein $R^5$ and $R^6$ together with the carbon atom to which they are attached form a $C_3$-$C_6$-cycloalkyl group; wherein the cycloalkyl group is optionally substituted with from 1 to 4 $R^{12}$ groups.
22. A herbicidal composition of claim 21, wherein $R^5$ and $R^6$ together with the carbon atom to which they are attached form a cyclopropyl group; wherein the cyclopropyl group is optionally substituted with from 1 to 4 $R^{12}$ groups.
23. A herbicidal composition of claim 16, wherein the compound of formula (I) is selected from:

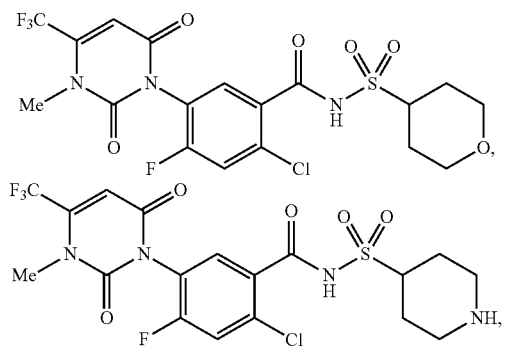

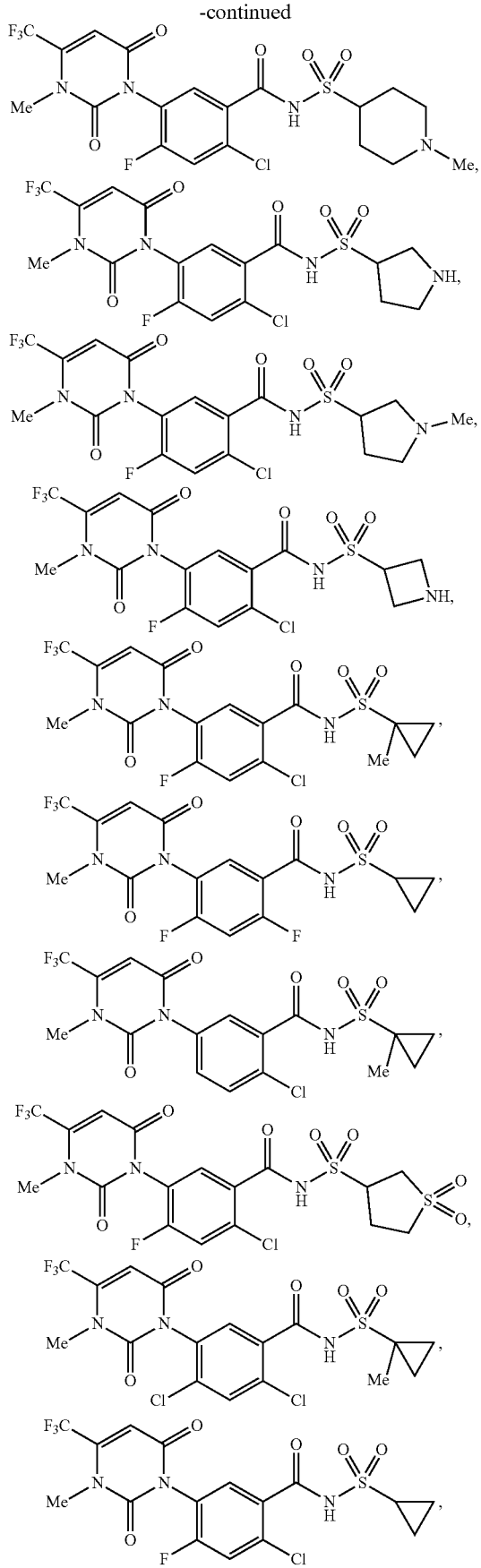
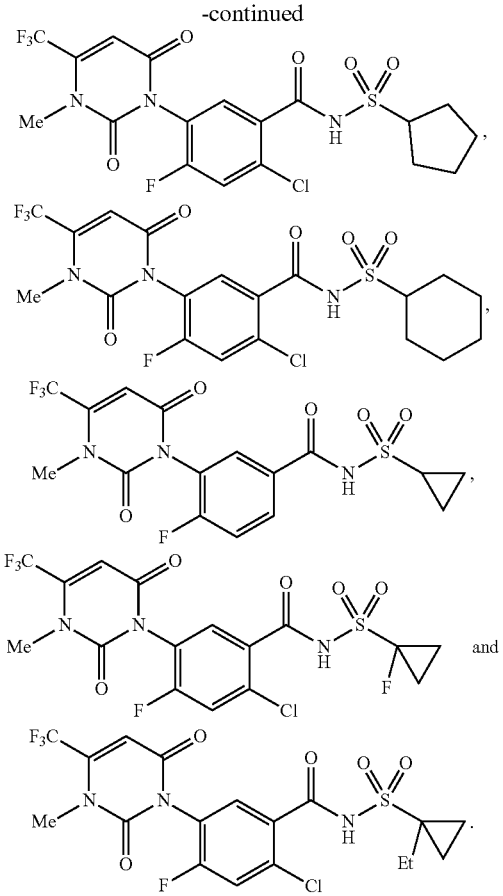
24. A herbicidal composition of claim 23, wherein the compound of formula (I) is:
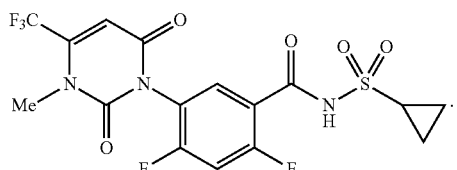
25. A herbicidal composition of claim 23, wherein the compound of formula (I) is:
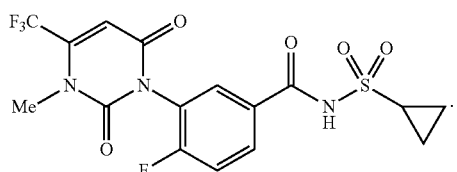
26. A herbicidal composition of claim 23, wherein the compound of formula (I) is: